US008415117B2

(12) United States Patent
Jalan et al.

(10) Patent No.: US 8,415,117 B2
(45) Date of Patent: Apr. 9, 2013

(54) PROGNOSIS AND THERAPY OF LIVER FAILURE

(75) Inventors: Rajiv Jalan, London (GB); Rajeshwar P Mookerjee, London (GB); Vanessa Stadlbauer, London (GB); Nathan Davies, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 12/311,605

(22) PCT Filed: Oct. 29, 2007

(86) PCT No.: PCT/GB2007/004107
§ 371 (c)(1),
(2), (4) Date: Jun. 19, 2009

(87) PCT Pub. No.: WO2008/050144
PCT Pub. Date: May 2, 2008

(65) Prior Publication Data
US 2010/0297018 A1 Nov. 25, 2010

(30) Foreign Application Priority Data

Oct. 27, 2006 (GB) .................................. 0621454.8

(51) Int. Cl.
*C12Q 1/02* (2006.01)
*A61K 35/14* (2006.01)
(52) U.S. Cl. .......................................... 435/29; 424/534
(58) Field of Classification Search .................. None
See application file for complete search history.

(56) References Cited

U.S. PATENT DOCUMENTS

| 5,476,715 A | 12/1995 | Otto |
| 5,998,389 A | 12/1999 | Loverock |
| 2004/0228829 A1 | 11/2004 | Roberts et al. |

FOREIGN PATENT DOCUMENTS

| EP | 0 129 786 | 2/1990 |
| JP | 2005-533483 | 11/2005 |
| SU | 784869 A1 | 8/1977 |
| WO | WO 96/41183 | 12/1996 |
| WO | WO 01/23413 A1 | 4/2001 |
| WO | WO 03/057730 A1 | 7/2003 |
| WO | WO 2004/071465 A2 | 8/2004 |

OTHER PUBLICATIONS

Panasiuk et al. Phagocytic and Oxidative Burst Activity of Neutrophils in the End Stage of Liver Cirrhosis; World Journal of Gastroenterology, vol. 11, No. 48 (2005) pp. 7661-7665.*
Mookerjee et al. Neutrophil Dysfunction in Alcoholic Hepatitis Superimposed on Cirrhosis is Reversible and Predicts the Outcome; Hepatology, vol. 46, No. 3 (Aug. 6, 2007) pp. 831-840.*
Trevisani et al. Impaired Tuftsin Activity in Cirrhosis: Relationship With Splenic Function and Clinical Outcome; Gut, vol. 50 (2002) pp. 707-712.*
Phagotest—Test Kit for the Quantification of Phagocytic Activity of Monocytes and Granulocytes in Heparinized Whole Blood. Downloaded from http://www.icp.ucl.ac.be/mexp/phagotst.pdf on Dec. 28, 2011.*
Cholongitas et al. Risk Factors, Sequential Organ Failure Assessment and Model for End-Stage Liver Disease Scores for Predicting Short Term Mortality in Cirrhotic Patients Admitted to Intensive Care Unit; Alimentary Pharmacology and Therapeutics, vol. 23 (Apr. 2006) pp. 883-893.*
Fujimoto et al., "Plasma Endotoxin and Serum Cytokine Levels in Patients with Alcoholic Hepatitis: Relation to Severity of Liver Disturbance," *Alcoholism, Clinical & Exper. Research*, vol. 24, No. 4, pp. 48S-54S (2000).
Stadlbauer et al., "Ex Vivo Endotoxin Removal from Plasma Restores Neutrophil Function," *Journ. of Hepatology, Munksgaard Intern. Publ.*, vol. 46, pp. S87 (2007).
International Search Report for PCT/GB2007/004107 completed Jan. 31, 2008, 6 pgs.
Written Opinion of the International Searching Authority for PCT/GB2007/004107, completed Jan. 31, 2008, 12 pgs.
Homann et al., "Ascites Fluid and Plasma Calprotectin Concentrations in Liver Disease," *Scand. J. Gastoenterol.*, 2003, vol. 4, pp. 415-420 (2003).
Stanley et al., "Neutrophil Activation in Chronic Liver Disease," *Euro. Journ. of Gastroenterol. & Hepatology*, vol. 8, pp. 135-138 (1996).
Mookerjee et al., "Pre-primed Neutrophil Oxidative Burst is Independent of Clinical Severity and Outcome in Patients with Severe Alcoholic Liver Disease," *Hepatology*, p. 236A (2003).
De Fernandez et al., "Neutrophil Phagocytic and Bactericidal Function in Primary Biliary Cirrhosis and other Chronic Liver Diseases," *Clin. Exp. Immunol.*, vol. 67, pp. 655-661 (1987).
Campbell et al., Neutrophil Function in Chronic Liver Disease, Clin. Exp. Immunol., vol. 45, pp. 81-89 (1981).
ORPEGEN Phartma-Phagoburst (RTM), http://www.orpegen.com/en/products/diagnostics/phagoburst_description.php, pp. 1-3, (2007).
Appen et al., "Microspheres Based Detoxification System: A New Method in Convective Blood Purification," *Artificial Organs*, vol. 20, No. 5, pp. 420-425 (1996).
Staubach et al, "A New Endotoxin Adsorption Device in Gram-Negative Sepsis: Use of Immobilized Albumin with the Matisse® Adsorber," *Transfusion and Apheresis Science*, vol. 29, pp. 93-98 (2003).
Alba et al., "Stimulators of AMP-activated Protein Kinase Inhibit the Respiratory Burst in Human Neutrophils," *FEBS Letters*, vol. 573, pp. 219-225 (2004).

(Continued)

Primary Examiner — Rebecca Prouty
Assistant Examiner — Paul Martin
(74) Attorney, Agent, or Firm — Foley & Lardner LLP

(57) ABSTRACT

A method for assessing prognosis in an individual suffering from liver failure, which method comprises detecting endotoxin in the individual, for example by determining the neutrophil function in the individual. The method can be used to determine whether there is an increased risk of infection in the individual, an increased risk of organ failure in the individual, an increased risk of mortality in the individual and/or an increased risk that the individual will not respond positively to treatment with an immunosuppressive agent, a steroid or an antibiotic.

11 Claims, 8 Drawing Sheets

OTHER PUBLICATIONS

Aggarwal et al., "Predictors of Mortality and Resource Utilization in Cirrhotic Patients Admitted to the medical ICU," *Chest*, vol. 119, pp. 1489-1497 (2001).

Bohmer et al., "Dose Effects of LPS on Neutrophils in a Whole Blood Flow Cytometric Assay of Phagocytosis and Oxidative Burst," *Cytometry*, vol. 13, pp. 525-531 (1992).

Condliffe et al., "Neutrophil Priming: Pathophysiological Consequences and Underlying Mechanisms," *Clinical Science*, vol. 94, pp. 461-471 (1998).

DeLeo et al., "Neutrophils Exposed to Bacterial Lipopolysaccharide Upregulate NADPH Oxidase Assembly," *The Journ. of Clinical Invest.*, vol. 101, No. 2, pp. 455-463 (1998).

Etheredge et al., "Chronic Endotoxemia Reversibly Alters Respiratory Burst Activity of Circulating Neutrophils," *Journ. of Surgical Research*, No. 55, pp. 261-268 (1993).

Felver et al., "Plasma Tumor Necrosis Factor α Predicts Decreased Long-Term Survival in Severe Alcoholic Hepatitis," *Alcoh. Clin. & Exper. Res.*, vol. 14, No. 2, pp. 255-259 (1990).

Garcia-Tsao et al., "Gut Microflora in the Pathogenesis of the Complications of Cirrhosis," *Best Prac. Res. Clin. Gast.*, vol. 18, No. 2, pp. 353-372 (2004).

Jaeschke et al., "Role of Neutrophils in Acute Inflammatory Liver Injury," *Liver Intern.*, vol. 26, pp. 912-919 (2006).

Lumsden et al., "Endotoxin Levels Measured by a Chromogenic Assay in Portal, Hepatic and Peripheral Venous Blood in Patients with Cirrhosis," *Hepatology*, vol. 8, pp. 232-236 (1988).

Mathurin et al., "Survival and Prognostic Factors in Patients with Severe Alcoholic Hepatisis Treated with Prednisolone," *Gastroenterology*, vol. 110, pp. 1847-1853 (1996).

Mathurin et al., "Corticosteroids Improve Short-Term Survival in Patients with Severe Alcoholic Hepatitis (AH): Individual Data Analysis of the Last Three Randomized Placebo Controlled Double Blind Trials of Corticosteroids in Severe AH," *Journ. of Hepatol.*, vol. 36, pp. 480-487 (2002).

McClain et al., "Increased Tumor Necrosis Factor Production by Monocytes in Alcoholic Hepatitis," *Hepatol.*, vol. 9, pp. 349-351 (1989).

Menon et al., "A Pilot Study of the Safety and Tolerability of Etanercept in Patients with Alcoholic Hepatitis," *Amer. Journ. of Gastroenterology*, vol. 99, pp. 255-260 (2004).

Naveau et al., "A Double-Blind Randomized Controlled Trial of Infliximab Associated with Prednisolone in Acute Alcoholic Hepatitis," vol. 39, pp. 1390-1397 (2004).

Prytz et al., "Portal Venous and Systemic Endotoxaemia in Patients without Liver Disease and Systemic Endotoxaemia in Patients with Cirrhosis," *Scand. J. Gastroenterol.*, vol. 11, pp. 857-863 (1976).

Rajkovic et al., "Mechanisms of Abnormalities in Host Defences Against Bacterial Infection in Liver Disease," *Clinical Science*, vol. 68, pp. 247-253 (1985).

Runyon, "Management of Adult Patients with Ascites Due to Cirrhosis," *Hepatology*, vol. 39, pp. 841-856 (2004).

Taieb et al., "Blood Neutrophil Functions and Cytokine Release in Severe Alcoholic Hepatitis: Effect of Corticosteroids," *Journ. of Hepatology*, vol. 32, pp. 579-586 (2000).

Thalheimer et al., "Infection, Coagulation, and Variceal Bleeding in Cirrhosis," *Gut*, vol. 54, pp. 556-563 (2005).

Tilg et al, "Anti-tumor Necrosis Factor-Alpha Monoclonal Antibody Therapy in Severe Alcoholic Hepatitis," *Journ. of Hepatology*, No. 38, pp. 419-425 (2003).

Urbaschek et al., "Endotoxin, Endotoxin-Neutralizing-Capacity, sCD14, sICAM-1, and Cytokines in Patients with Various Degrees of Alcoholic Liver Disease," *Alcohol Clin. Exp. Res.*, vol. 25, No. 2, pp. 261-268 (2001).

Brunt et al., "Nonalcoholic Steatohepatitis: A Proposal for Grading and Staging the Histological Lesions," *Am. J. Gastroenterol.*, vol. 94, pp. 2467-2474 (1999).

Christensen et al., "Glucocorticoids are Ineffective in Alcoholic Hepatitis: A Meta-Analysis Adjusting for Confounding Variables," *Gut*, vol. 37, pp. 113-118 (1995).

Fernandez et al., "Bacterial Infections in Cirrhosis: Epidemiological Changes with Invasive Procedures and Norfloxacin Prophylaxis," *Hepatology*, vol. 35, pp. 140-148 (2002).

Hanasawa, "Extracorporeal Treatment for Septic Patients: New Adsorption Technologies and Their Clinical Application," *Ther. Apher.*, vol. 6, No. 4, pp. 290-295 (2002).

Kamath et al., "A Model to Predict Survival in Patients with End-Stage Liver Disease," vol. 33, pp. 464-470 (2001).

Linderoth et al., "Short-term Prognosis of Community-Acquired Bacteremia in Patients with Liver Cirrhosis or Alcoholism: A Population-Based Cohort Study," *Alcohol. Clin. Exp. Res.*, vol. 30, No. 4, pp. 636-641 (2006).

Maddrey et al., "Corticosteroid Therapy of Alcoholic Hepatitis," *Gastroenterology*, vol. 75, pp. 193-199 (1978).

Navasa, et al., "Bacterial Infections in Liver Cirrhosis," *Ital. J. Gastro.*, vol. 31, pp. 616-625 (1999).

Such et al., "Detection and Identification of Bacterial DNA in Patients with Cirrhosis and Culture-Negative, Nonneutrocytic Ascites," *Hepatology*, vol. 36, pp. 135-141 (2002).

Verma et al., "Prevalence of Septic Events, Type 1 Hepatorenal Syndrome, and Mortality in Severe Alcoholic Hepatitis and Utility of Discriminant Function and MELD Score in Predicting These Adverse Events," *Dig. Dis. Sci.*, vol. 51, pp. 1637-1643 (2006).

Rolando et al., "Granulocyte Colony-Stimulating Factor Improves Function of Neutrophils from Patients with Acute Liver Failure," *European Journ. of Gastroenterology & Hepatology*, vol. 12, No. 10, pp. 1135-1140, (2000).

Notice of Reasons for Rejection cited in related Japanese Patent Application No. 2009-533946, dated Jan. 24, 2012.

Fiuza et al., "In Vivo Neutrophil Dysfunction in Cirrhotic Patients with Advanced Liver Disease," *The Journ. of Infectious Diseases*, vol. 182, pp. 526-533 (2000).

Kirsch et al., "Liver Cirrhosis and Portal Hypertension," *Journ. of Gastroenterology and Hepatology*, vol. 15, pp. 1298-1306 (2000).

Maderazo et al., "Defective Regulation of Chemotaxis in Cirrhosis," *J. Lab. Clin. Med.*, vol. 85, pp. 621-630 (1975).

Pascual et al., "Effect of Plasma and LPS on Respiratory Burst of Neutrophils in Septic Patients," *Intensive Care Med.*, vol. 24, pp. 1181-1186 (1998).

Rajkovic et al., "Abnormalities of Neutrophil Phagocytosis, Intracellular Killing and Metabolic Activity in Alcoholic Cirrhosis and Hepatitis," *Hepatology*, vol. 6, No. 2, pp. 252-262 (1986).

Rajkovic et al., "Polymorphonuclear Leucocyte Locomotion and Aggregation in Patients with Alcoholic Liver Disease," *Clin. Exp. Immunol.*, vol. 58, pp. 654-662 (1984).

Van Epps et al., "Inhibitors of Leukocyte Chemotaxis in Alcoholic Liver Disease," *The Amer. Journ. of Medicine*, vol. 59, pp. 200-207 (1975).

Wyke et al., "Impaired Opsonization by Serum from Patients with Chronic Liver Disease," *Clin. Exp. Immunol.*, vol. 51, pp. 91-98 (1983).

Yousif-Kadaru et al., "Defects in Serum Attractant Activity in Different Types of Chronic Liver Disease," *Gut*, vol. 25, pp. 79-84 (1984).

\* cited by examiner

PROGNOSIS AND THERAPY OF LIVER FAILURE

CROSS-REFERENCE TO RELATED APPLICATIONS

This application is the National Phase of International Patent Application No. PCT/GB2007/004107, filed on Oct. 29, 2007, which claims the benefit of priority from Great Britain Application No. 0621454.8, filed on Oct. 27, 2006. The contents of these applications are incorporated herein by reference in their entirety.

FIELD OF THE INVENTION

The invention relates to a method for assessing liver function, in particular for predicting the clinical outcome of liver failure. It also relates to a kit for use in such a method and to the treatment of an individual identified as at risk of deleterious outcome using the method.

BACKGROUND TO THE INVENTION

Data from a European registry of liver failure suggests the incidence of liver disease is increasing with currently about 1 million patients with liver failure in Western Europe, a significant proportion secondary to alcohol. In the majority of patients, liver failure is the result of a precipitating event such as infection or alcoholic hepatitis on the background of established chronic liver disease; an entity that is referred to as "acute-on-chronic liver failure (ACLF)". Once liver failure is established, specific treatments are limited to organ support and mortality rates approach 50%. In patients with ACLF secondary to severe alcoholic hepatitis (AH), approximately 40% of deaths are thought to result from sepsis.

SUMMARY OF THE INVENTION

The inventors examined patients with alcoholic liver disease and have discovered a humoral factor, present in plasma, that destroys immune function in such patients. The removal of endotoxin leads to the restoration of function, suggesting that the humoral factor is an endotoxin-like molecule. Detection of this endotoxin-like molecule in those patients may be used to assess their clinical prognosis, in particular, risk of infection, risk of mortality, risk of organ failure and the likelihood that they will respond to conventional therapies such as immunosuppressive treatment.

In accordance with the present invention, there is therefore provided a method for assessing prognosis in an individual suffering from liver failure, which method comprises detecting endotoxin in the individual. The inventors have established that the humoral factor is capable of promoting neutrophil activation. The presence of the endotoxin-like molecule can be determined by assessing the neutrophil function of the individual. Accordingly, abnormal neutrophil function, such as neutrophil activation or decreased neutrophil phagocytic ability, represent important biological markers of deleterious outcome of liver failure. These markers may be used as a reliable predictor of progression and outcome in patients with liver failure.

Also provided is a test kit suitable for use in a method for assessing prognosis in an individual suffering from liver failure, which test kit comprises means for determining the level of neutrophil function in the individual.

The Examples demonstrate that addition of endotoxin to normal plasma increases the level of neutrophil activation. Further, removal of endotoxin from the plasma of patients with a high level of neutrophil activation is capable of reducing the level of neutrophil activation.

Accordingly, the invention further provides:
A test kit suitable for use in a method for assessing prognosis in an individual suffering from liver failure, which test kit comprises means for detecting endotoxin in the individual.
A method for the treatment of liver failure in an individual, which method comprises:
  (i) determining the prognosis of the individual using a method by a method of the invention; and
  (ii) reducing the level of endotoxin in the blood of an individual identified in (i) as at increased risk of infection, organ failure and/or mortality and/or at an increased risk that the individual will not respond positively to treatment with an immunosuppressive agent, a steroid or an antibiotic.
Use of an agent in the manufacture of a medicament for use in a method of treatment of liver failure in an individual, wherein the individual has been identified by a method of the invention as having an increased risk of infection, organ failure and/or mortality and/or an increased risk that the individual will not respond positively to treatment with an immunosuppressive agent, a steroid or an antibiotic, wherein the agent reduces the level of endotoxin in the blood of the individual.
Products containing:
  (i) means for determining neutrophil function in an individual; and
  (ii) an agent which reduces the level of endotoxin in the blood, as a combined preparation for simultaneous, separate or sequential use in a method of treatment of the human or animal body by therapy.

|  | Day | | | |
| --- | --- | --- | --- | --- |
|  | 20 | 40 | 60 | 80 |
| Events | 4 | 5 | 10 | 12 |
| At risk | 50 | 44 | 36 | 33 |

Figure 5:
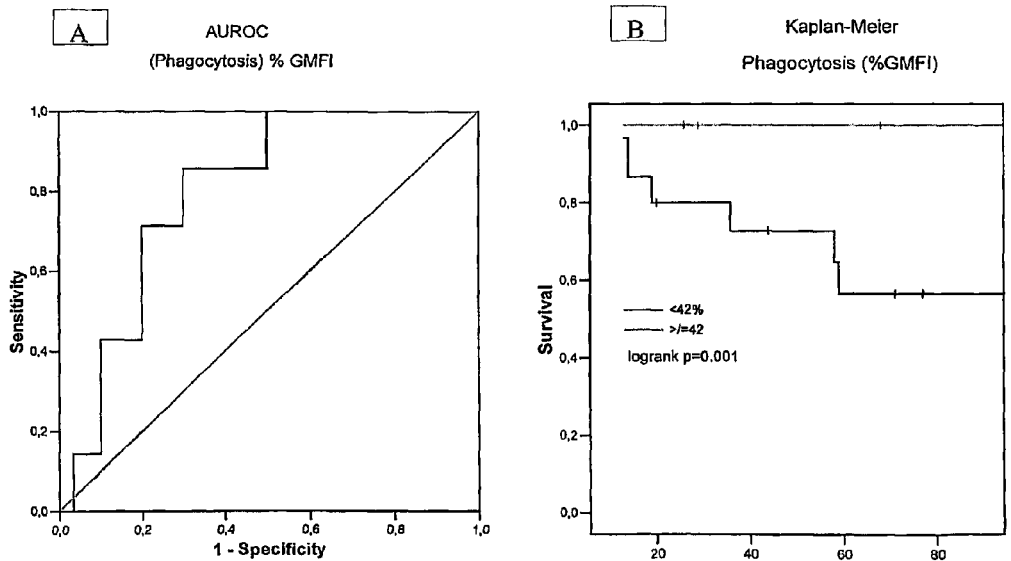

FIG. 5: (A) Area under the receiver operating curve to determine the predictive utility of measurement of the geometric mean of fluorescence intensity (GMFI) in determining survival. A cutoff of GMFI<295% had a sensitivity of 86% and a specificity of 76% for predicting death. Area=0.80; Std. Error=0.08; significance=0.002; cut-off=42; sensitivity=0.86; specificity=0.70. (B) Kaplan Meier survival curve and log-rank analysis for patients stratified for low (<295) or high (>/=295) GMFI.

|  | Day | | | |
| --- | --- | --- | --- | --- |
|  | 20 | 40 | 60 | 80 |
| Events | 4 | 4 | 5 | 5 |
| At risk | 29 | 29 | 26 | 24 |

Figure 6:
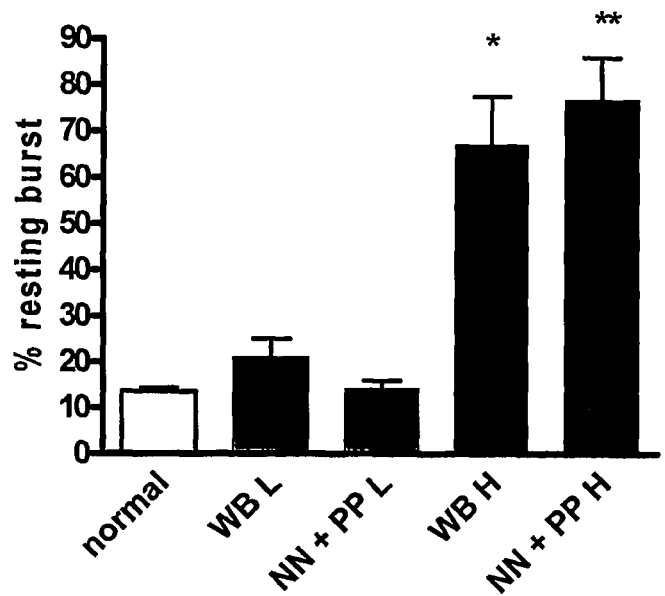

FIG. 6: Resting oxidative burst in whole blood of patients and in normal neutrophils incubated with patients plasma. Plasma from patients with high burst also induced a high burst in normal neutrophils, whereas plasma from patients with low resting burst failed to do so. WB whole blood, NN normal neutrophils, PP patients plasma, H high resting burst (>/=55%), L Low resting burst (<55%). * p=0.002 versus normal. ** p=0.0005 versus normal.

Figure 7:
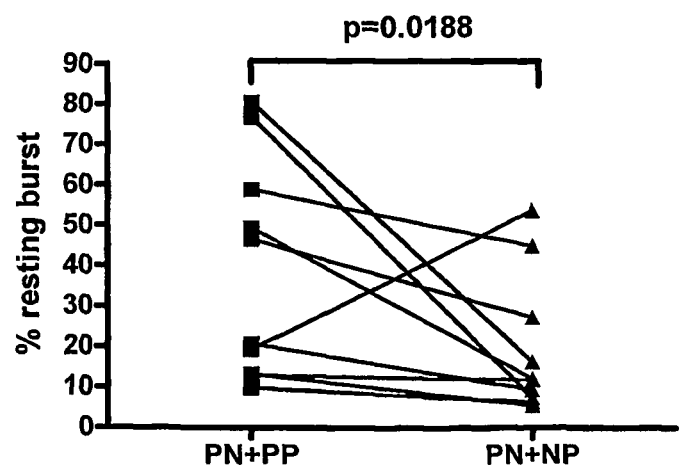

FIG. 7: Reversibility of resting oxidative burst by incubation of patients neutrophils with normal plasma. PN patient neutrophils, PP patient plasma, NP normal plasma.

Figure 8:
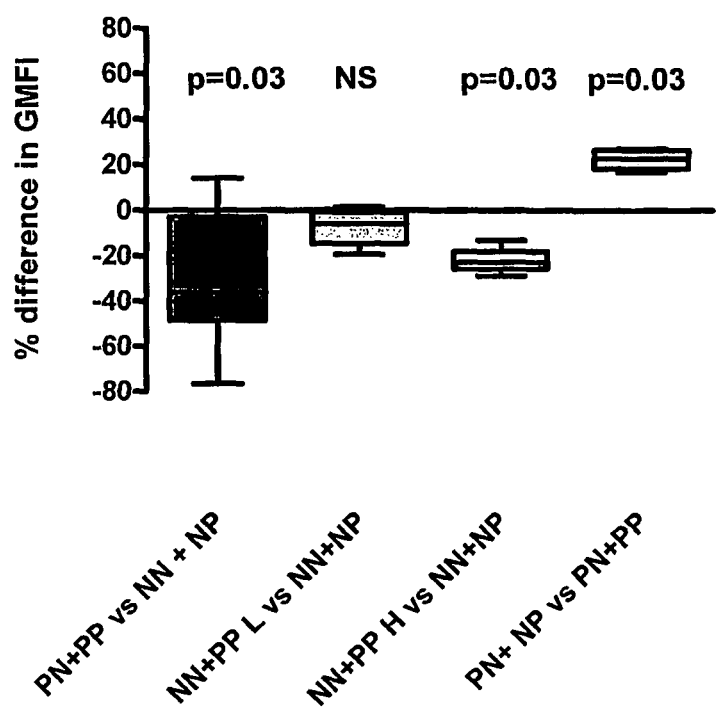

FIG. 8: Influence of plasma on phagocytosis. Patient neutrophils incubated in their own plasma show decreased phagocytosis. Incubation of normal neutrophils with plasma from patients with low resting burst does not change phagocytosis, plasma from patients with high burst decreases phagocytosis. Incubation of patient neutrophils with normal plasma restores phagocytic function. PN patient neutrophils, PP patient plasma, NN normal neutrophils, NP normal plasma, H high resting burst, L low resting burst.

Figure 9:
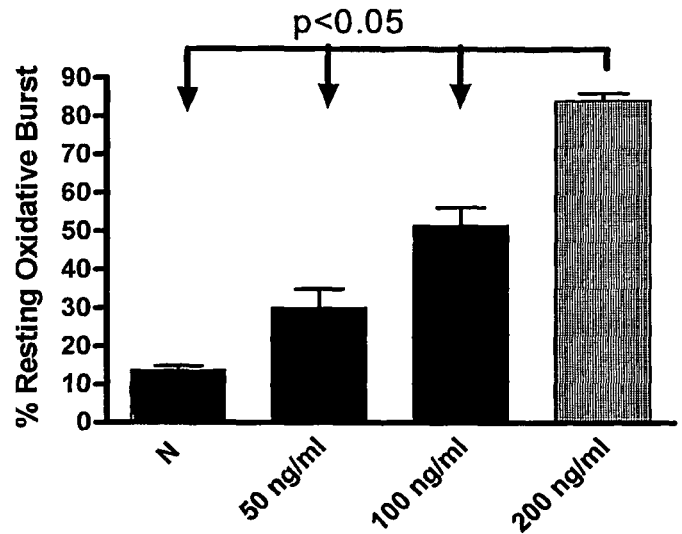

FIG. 9 Dose dependent increase in resting burst through incubation with endotoxin. * p<0.05; ** p<0.001.

Figure 10:
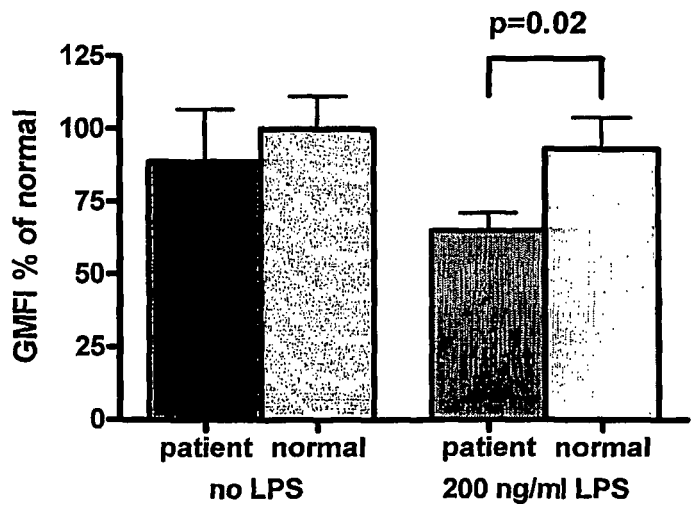

FIG. 10 Incubation with endotoxin does not change phagocytosis in normal neutrophils but decreases phagocytosis further in patients neutrophils.

Figure 11:
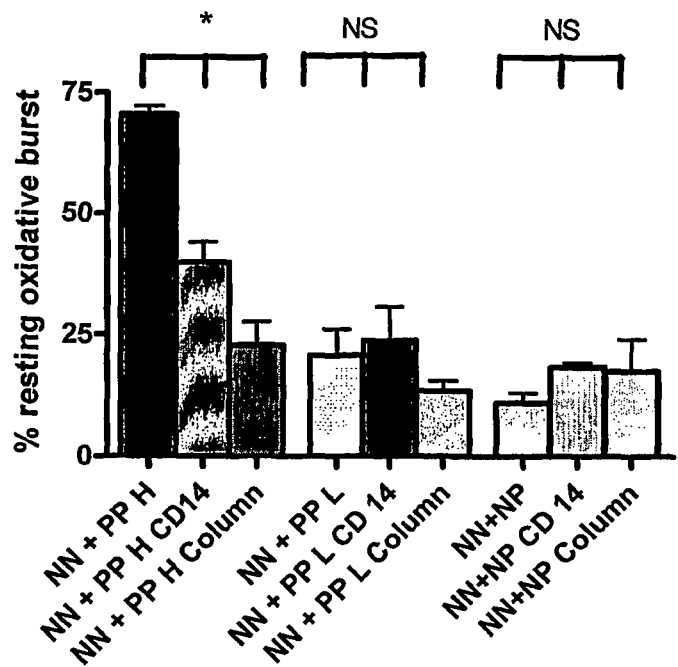

FIG. 11: Resting oxidative burst is reversible by passing plasma over an endotoxin-removal column or incubation with CD14 antibodies. The columns or the CD14 antibodies do not influence resting burst when plasma from patients with low burst or control plasma is used. NN+PP H vs NN+PP H CD14 p<0.001. NN+PP H vs NN+PP H Column p<0.001.

Figure 12:
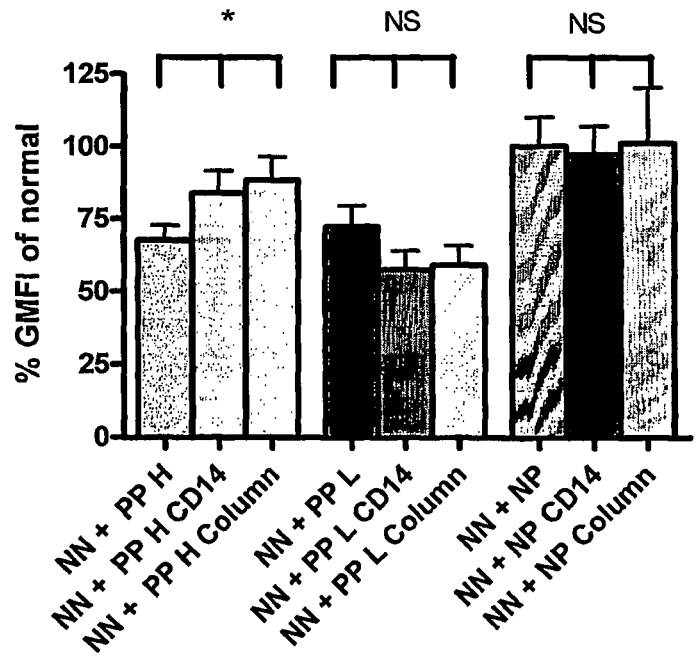

FIG. 12: decreased phagocytosis is reversible by passing plasma over an endotoxin-removal column or incubation with CD14 antibodies. The columns or the CD14 antibodies do not influence resting burst when plasma from patients with low burst or control plasma is used. NN+PP H vs NN+PP H CD14 p=0.004 NN+PP H vs NN+PP H Column p=0.03.

Figure 13:
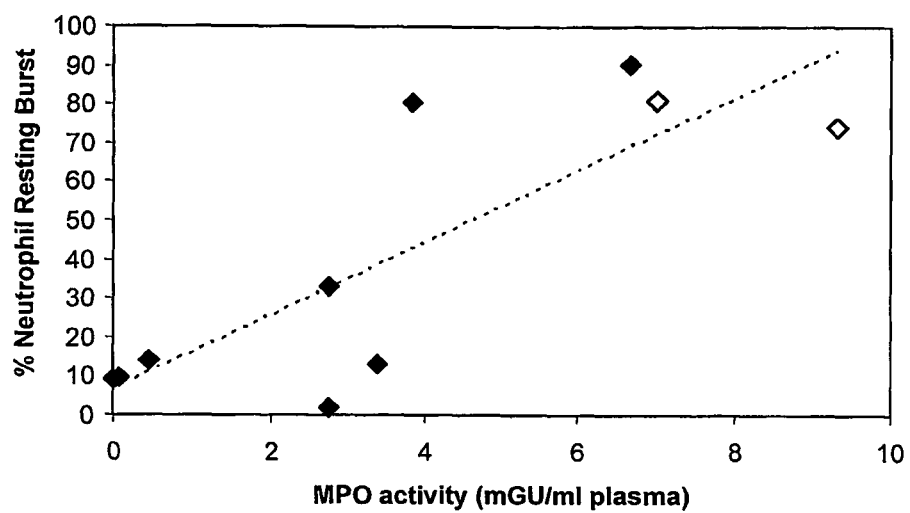

FIG. 13: shows the relationship between neutrophil resting burst (%) and plasma (cell free) myeloperoxidase (MPO) activity, expressed in guaiacol units x$10^{-3}$ (mGU) per milliliter plasma in 10 patients with varying severity of liver disease. The fit by linear regression is indicated, showing a significant relationship between these two measures (p=0.0075, $r^2$=0.66). The two subjects that subsequently died are indicated with hollow symbols.

DETAILED DESCRIPTION OF THE INVENTION

Throughout this specification, the word "comprise", or variations such as "comprised" or "comprising", will be understood to imply the inclusion of a stated element, integer or step, or group of elements, integers or steps, but not the exclusion of any other element, integer or step, or group of elements, integers or steps.

The reference to any prior art in this specification is not, and should not be taken as, an acknowledgement or any form of suggestion that that prior art forms part of the general knowledge in Australia or elsewhere.

The current strategies for the treatment of alcoholic hepatitis include administration of immunosuppressive agents such as steroids and more recently anti-TNF strategies have been used. The data for the use of these drugs in alcoholic hepatitis are conflicting and although steroids are widely used, there is considerable heterogeneity in the results of the existing clinical trials. Similarly, the use of anti-TNF strategies in alcoholic hepatitis in patients has been shown to have a positive effect in some studies whereas increased infection risk (and mortality) has resulted in stoppage of the clinical trial in other studies.

There is thus a need to identify which patients are likely to respond to which therapeutic treatments. There is a particular need to identify whether particular patients are at higher risk of infection, organ failure and/or mortality and whether particular treatments may increase these risks.

The inventors have determined that the detection or measurement of endotoxin or endotoxin activity in plasma or whole blood from liver disease patients allows the classification of those patients into low risk or high risk groups. This allows prediction of the prognosis of a patient. In particular, this allows the determination of the relative risk of mortality, risk of infection and risk of organ failure in patients with liver failure. Assessment of endotoxin or endotoxin activity may also help define assignment to a specific therapy. This can be used to determine whether a patient should be treated with, for example, antibiotics, corticosteroids, anti-TNF or extracorporeal therapy. This can also be used to predict whether such therapies are likely to lead to unwanted side effects, such as an increased risk of infection. This information can be used by a physician in order to make a clinical decision as to how best to treat an individual patient.

The inventors have demonstrated that the use of such measurements acts as a reliable predictor of outcome in patients with severe alcoholic hepatitis. It is believed that application of a test as described herein helps define those patients in whom treatment with immunosuppressive agents, such as steroids or anti-TNF strategies, will be effective. This will also help define those other patients in which such immunosuppressive therapies may lead to an increased risk of infection. It is also believed that application of this test helps define those patients with progressive liver failure in whom early intervention with liver support systems is warranted, compared with currently available prognostic scores (DF, MELD, Child-Pugh). Its use may also be expanded to a population of patients awaiting transplantation to stratify utilization of organs for transplantation or to determine organ function after orthotopic liver transplantation.

The presence of the endotoxin-like humoral factor can be assessed by detecting the factor directly, for example by detecting the presence of endotoxin, or it can be assessed by detecting the factor indirectly. For example, a method may comprise detecting endotoxin activity as an indicator of the presence of such a humoral factor, or detecting a downstream effect caused by the presence of the humoral factor.

Throughout this document, the terms humoral factor, transmissible factor, endotoxin-like factor and endotoxin are used interchangeably to describe the factor identified in the Examples in patients having liver disease. These terms are intended to refer to a factor that can be found in the blood or plasma of such patients, that is transmissible and that has endotoxin activity.

The humoral factor can be transmitted in plasma. That is, neutrophil activation can be caused in a population of normal neutrophils by exposure to plasma which has been in contact with a population of activated neutrophils. For example, as demonstrated in the Examples, the humoral factor can cause activation of neutrophils that were not previously activated. A method for detecting endotoxin (humoral factor) may therefore involve contacting plasma from the individual with a sample of normal neutrophils not from that individual and determining whether this causes abnormal function, such as activation, in those neutrophils. The neutrophils may be any sample of normal neutrophils as described herein. For example, the neutrophils may be from an individual who does not have liver failure, they may be from a population of neutrophils which has been previously tested and shown to have normal function, for example shown not to be activated, or they may be from a neutrophil cell line. Neutrophil function such as neutrophil activation may be measured by any of the methods described herein, for example by assessing oxidative burst or MPO levels. Such an assay may be carried out on a sample of plasma from the individual and may be carried out in vitro.

The presence of a factor in the plasma of an individual suffering from liver failure, which factor is capable of activating neutrophils, is indicative that the individual themself has activated neutrophils and is indicative that the individual may be classified as high risk as described herein.

The Inventors have demonstrated that the transmissible activity of the humoral factor in plasma is removable by endotoxin removal. Similarly, activation of neutrophils can be stimulated by exposing those neutrophils to endotoxin.

The assays relating to the transmissible factor may therefore be adapted to the detection of endotoxin or its effects. For example, the assays may detect the presence of endotoxin in plasma from the individual, or specific effects of that endotoxin. The presence or activity of endotoxin may be detected using methods known in the art.

Measurement of endotoxin activity may be achieved in a variety of ways. For example, a method of the invention may comprise assessing the neutrophil function of the individual. As described herein, numerous methods may be used to assess the function of neutrophils. This may be done by assessing the ability of the neutrophils to phagocytose; or their ability to carry out other essential neutrophil functions such as oxidative burst or degranulation. Specific biochemical effects of neutrophil activation may also be assessed, such as release of reactive oxidants or production of hypochlorous acid following MPO activation by a population of neutrophils.

The presence of, or amount of, endotoxin may be assessed in a variety of ways. This will involve the detection of, and/or measurement of, endotoxin, an endotoxin activity, or a downstream effect of endotoxin, and a comparison with the presence, amount, or level of endotoxin, endotoxin activity or a downstream effect of endotoxin in a normal individual. For example, this may involve the detection of, and/or measurement of a function of neutrophils in the individual and a comparison with the same or equivalent function in normal neutrophils. For example, endotoxin presence, amount or effect, such as neutrophil function, in a sample from an individual having liver failure may be compared with endotoxin presence, amount or effect, such as neutrophil function, in a control sample, such as a sample (e.g. of neutrophils) that is not from that individual. The control sample for comparison may be from an individual that does not have liver disease or an individual that does not have liver failure, such as an individual that has normal liver function. Such a comparison with a normal sample such as normally functioning neutrophils will allow an assessment of whether endotoxin levels (e.g. neutrophil function) in the individual with liver failure are normal, and the individual is thus at low risk for the factors described herein, or whether endotoxin levels (e.g. neutrophil function) are abnormal, and the individual is thus at high risk for the factors described herein.

In some assays, the proportion of neutrophils in a sample reacting in a particular way may be assessed. In other assays, the overall reaction of a population may be quantified. In other assays, the average reaction of individuals within a population of neutrophils may be assessed. In yet further assays, the presence or absence of specific factors in a sample may be assessed or quantified.

Where the assay involves quantification of a measure of endotoxin presence, activity or effect, such as neutrophil function, a comparison of the quantity obtained in relation to an individual having liver disease may be compared with the quantity obtained for a control. Where the quantities are the same or similar, endotoxin in the individual may be considered normal and the individual classified as low risk. A quantity that is similar to a control may differ from the control by less that 1%, less than 2%, less than 5%, less than 10% or less than 20%. Where the quantities are different, endotoxin in the individual may be considered abnormal and the individual classified as at high risk. A quantity that is different to a control may differ from the control by more than 1%, more than 2%, more than 5%, more than 10% or more than 20%. A suitable threshold for assessing whether a difference exists may be determined based on the particular assay being used. For example, where an assay has a high degree of variability between control samples, a greater variance from the control may be considered a difference in accordance with the invention. Where an assay has less variability and control samples show greater consistency, a smaller difference from the control may be considered such a difference.

As explained further below, it may not be necessary to carry out a direct comparison of liver failure samples (e.g. neutrophils) and normal samples (e.g. neutrophils) on every occasion. For some tests it will be possible to set a threshold or cut-off level based on results obtained from a number of individuals. The results obtained from an individual may then be compared with that threshold or cut-off level, rather than with another sample, in order to determine whether the endotoxin (e.g. neutrophil function) is normal or abnormal, and whether the individual is classified as at high risk or low risk.

In one aspect, the neutrophil function is the level of activation of the neutrophils. An increased level of neutrophil activation compared with neutrophils from a normal control is indicative that the individual is at high risk of the factors described herein. As shown in the Examples, the Inventors have found that in some individuals (classified as low risk), neutrophils are generally primed but not activated, whereas in other individuals (classified as high risk), neutrophils are generally activated. Primed neutrophils are ready to respond to a bacterial challenge. Priming of neutrophils involves functional and structural changes resulting in an increased response to a microbal challenge and is well described in the art. Activated neutrophils are also well described in the art. These include those neutrophils which have an exaggerated response to fMLP or a "high resting burst" as described herein.

Neutrophil activation may be assessed in a variety of ways. One approach assesses the ability of the neutrophils to generate a further oxidative burst, for example on challenge with a microbial agent such as bacteria. Any challenge that would normally lead to an oxidative burst reaction in neutrophils can be used in such an approach. For example, the challenge may be with bacteria such as fMLP.

The inventors have found that presentation of a new bacterial challenge to primed and activated neutrophils was associated with an inability of the cells to generate a further oxidative burst. Accordingly, the neutrophils of individuals who are classified as at high risk of the factors described herein will show a lesser response to such a challenge than the neutrophils of low risk individuals. A decreased oxidative burst response to such a challenge compared with the response of normal neutrophils is therefore indicative that the individual should be classified as high risk for the factors described herein. An oxidative burst response that is similar to the response by normal neutrophils is indicative that the individual should be classified as low risk for the factors described herein. This is believed to be because the resting level of oxidative burst is higher in the high risk group of individuals, so the challenge is unable to further increase the oxidative burst response.

Accordingly, neutrophil activation may be assessed by measuring the resting level of oxidative burst. This resting level will be higher in neutrophils from a high risk individual than in neutrophils from a low risk individual. An increased resting level of oxidative burst compared with the resting level of oxidative burst in normal neutrophils is therefore indicative that the individual should be classified as high risk for the factors described herein. A resting level of oxidative burst that is similar to that of normal neutrophils is indicative that the individual should be classified as low risk for the factors described herein.

Neutrophil activation may also be assessed by measuring the change in oxidative burst from its resting level upon a challenge as described above. As explained above, neutrophils with a high resting level of oxidative burst will not have the ability to respond as strongly to such a challenge. Neutrophils that are already activated will therefore show a reduced increase in oxidative burst from resting level on such a challenge when compared with normal neutrophils. A reduced increase in oxidative burst from resting level upon such a challenge is indicative that the individual should be classified as high risk for the factors described herein. An increase in oxidative burst from resting level upon such a challenge that is similar to that seen on challenge of normal neutrophils is indicative that the individual is at low risk for the factors described herein.

Activation of neutrophils, such as oxidative burst or neutrophil granule release, may be assessed in a variety of ways. This can be achieved by assessing changes in the neutrophils themselves or changes in the environment of the neutrophils that results from such activation. For example, this can be achieved by detecting the presence of substances that are released during oxidative burst or neutrophil granule release. Such substances can be detected directly, by detecting and/or measuring their presence, or indirectly by detecting and/or measuring the effects of such substances. These substances may be detected directly in the blood, in a fraction or extract of the blood, or in an in vitro solution comprising the neutrophils being tested. Substances that may be detected, directly or indirectly, include reactive oxidants, myeloperoxidase, hydrogen peroxide, defensins, bactericidal/permeability increasing protein (BPI) and the serine proteases neutrophil elastase and cathepsin.

Methods for detecting such substances are well known in the art. For example, the Phagoburst® kit (Orpegen Pharma, Heidelberg, Germany) uses dihydrorhodamine 123 to detect and measure the presence of reactive oxidants. The method of the invention may therefore involve addition of a reagent such as dihydrorhodamine 123 to a sample of neutrophils, and oxidation to detect the presence of, and amount of, reactive oxidants in the sample, either at resting state or upon challenge of the neutrophils. Any reagent capable of detecting reactive oxidants may be utilised and suitable detection steps can be selected depending on the reagent chosen.

An alternative method for detecting neutrophil activation detects the release of myeloperoxidase (MPO) into the plasma from neutrophils. For example, the CardioMPO™ test (PrognostiX Inc, Ohio, USA) uses a sandwich ELISA to measure MPO concentration in human plasma. MPO may thus be detected directly, or indirectly such as by assessing the level of hypochlorous acid formed in a sample of plasma following the addition of hydrogen peroxide. As shown in the Examples, MPO activity may be assessed by supplying hydrogen peroxide to a solution comprising plasma, guaiacaol and cetyltrimethylammoniumbromide and monitoring the reaction. The change in visible light absorbance at 470 nm can be used to calculate the rate of MPO activity. Such assays are particularly useful as they may be carried out on plasma rather than whole blood so they do not require the preservation of viable cells. Thus, the activity of myeloperoxidase released from neutrophils may be indirectly assessed by measuring its production of hypochlorous acid. The release of myeloperoxidase by neutrophils, either in a resting state or upon challenge, can thus be detected and/or quantified. An increased level of resting MPO activity or MPO release is indicative of an increased level of neutrophil activation.

As with other tests of neutrophil activation, substances released by degranulation such as MPO may be present at higher resting levels in activated neutrophils. The release of such substances in response to challenge may be reduced where the neutrophils are activated and the increase from resting level upon challenge may be less in a sample of activated neutrophils. Any of these effects suggesting the presence of activated neutrophils may indicate that the individual should be classified as high risk as described herein.

A further function of neutrophils that can be assessed according to the invention is neutrophil phagocytosis. The Inventors have observed that neutrophil phagocytosis is abnormal in individuals classified as high risk for the factors described herein. An individual having abnormal phagocytosis compared with phagocytosis by a normal population of neutrophils can therefore be classified as at high risk for the factors described herein. A similar level and degree of neutrophil phagocytosis is indicative that the individual should be classified as at low risk for the factors described herein. The Inventors observed that in high risk individuals, neutrophils were able to phagocytose bacteria in a similar way to healthy controls, but the number of bacteria phagocytosed by each neutrophil was significantly reduced compared to the normal neutrophil control. Individuals may therefore be classified as high risk if their neutrophils show such impaired ability to phagocytose. This may be indicated by an overall decrease in phagocytosis by a population of neutrophils, or by a decrease in the level of phagocytosis achieved by individual neutrophils.

A number of different approaches can be used to quantify or assess phagocytosis. For example, some methods will assess the overall number or proportion of neutrophils that show phagocytosis within a sample. This may provide an indication of the relative phagocytotic activity of different samples, as such samples may comprise populations of neutrophils that are actively phagocytosing, and populations of neutrophils that are not. Alternatively, some methods may assess the total amount of phagocytosis that is occurring in a sample, such as the number of bacteria that are phagocytosed when contacted with a given population of neutrophils. Such methods may provide an indication of the rate of killing of bacteria by a given neutrophil population. A rate of killing per neutrophil cell can also be determined on a sample by sample basis.

This may be assessed directly, by quantifying the level of phagocytosis achieved by such cells. This may be achieved by labelling material, such as cells, to be phagocytosed, allowing phagocytosis to occur and then quantifying and/or locating the label to indicate whether and how many cells have been phagocytosed by the neutrophils. For example, the Phagotest® kit (Orpegen Pharma, Heidelberg, Germany) uses FITC-labelled opsonized *C. coli* bacteria and can be used to measure the overall percentage of neutrophils showing phagocytosis and the number of bacteria engulfed per cell. A method of the invention may therefore quantify the number of neutrophils in a sample showing phagocytosis. A method of the invention may quantify the level of phagocytotis activity shown by individual neutrophils. This may be achieved by quantifying the number of cells that individual neutrophils, or a population of neutrophils are able to phagocytose.

In accordance with the present invention therefore neutrophil function is assessed in an individual. Preferably this is carried out in vitro or ex vivo on a sample from the individual. As explained herein, abnormal neutrophil function may be used as a predictor of disease progression in a patient with liver failure. Such abnormal function may be seen as increased activation of the neutrophil, such as an increased resting oxidative burst or increased resting degranulation, or as reduced oxidative burst or degranulation response to a challenge. As explained above, this may be detected by measuring the oxidative burst itself, or by measuring the presence or amount of substances released during such a burst. Abnormal neutrophil function may also be detected by reduced phagocytic activity. Patients in which increased neutrophil activation is seen, and patients in which reduced phagocytosis is seen, can be classified as at high risk of the factors described herein.

The indicators of abnormal neutrophil function may be quantified by comparing with the relative levels in individuals who are not suffering from liver disease. For example, a sample of neutrophils from an individual who is not suffering from liver disease or an individual who does not have liver failure may be used for comparison. Generally, the control neutrophils for comparison should be from a source in which the neutrophils are expected to be normal, e.g. from a population of neutrophils which have not been exposed to any factors which might activate them. The control population of neutrophils are preferably primed for response, but not activated. A number of such samples may be used to achieve an average "normal" level for the function being assessed. Using such an approach, it may be possible to set particular levels of, for example, neutrophil activation or phagocytose or other neutrophil function which will be particularly indicative of these clinical effects.

In accordance with the present invention, a determination of neutrophil function, such as the oxidative burst test or an assessment of the phagocytic ability of neutrophils, may be used to categorise individuals. Using these methods, individuals having liver failure may be categorised as being at high risk or at low risk of a variety of factors. As described above, individuals may be categorised in this way based on the function of their neutrophils.

Individuals in whom neutrophils are generally functioning in the same way as normal neutrophils (e.g. from an individual who does not have liver disease, in whom neutrophils are primed but not activated) are categorised as at low risk. These individuals have a lower risk of factors such as infection, organ failure and mortality. These individuals are more likely to respond to conventional liver failure therapies such as immunosuppressives, corticosteroids and antibiotics.

Individuals in whom the neutrophils are not functioning normally are categorised as high risk. As described herein, abnormal neutrophil function may be seen as, for example, increased neutrophil activation or decreased phagocytosis. Such neutrophils may be primed for response but already activated so unable to respond normally to challenge. Individuals in this category are at higher risk of infection, higher risk of organ failure and higher risk of mortality. The increased risk of organ failure and mortality in these individuals may be a direct result of the increased risk of infection. Such high risk individuals are also more likely to be non-responders to conventional treatments of liver disease, such as immunosuppressives, steroids and antibiotics. It is notable that in the studies carried out by the Inventors, this high risk group of patients had infection with multiple resistant unconventional organisms despite antibiotic therapy, often during the same hospital admission. Use of such treatments on high risk individuals may further increase the risk of infection in those individuals, and the potential consequences of such infection such as organ failure and mortality.

Accordingly, an abnormal neutrophil function in an individual with liver failure is indicative of an increased likelihood of infection, and/or organ failure, increased mortality and decreased likelihood that the patient will respond well to steroid, antibiotic or immunosuppressive treatment.

The results reported herein may also have important implications in the selection of patients having liver failure for immunosuppressive therapy. Although controversy exists around the use of corticosteriods and anti-TNF strategies for the routine treatment of liver disease such as alcoholic hepatitis, there is little doubt of their effectiveness in selected patients. The methods described herein may allow the selection of patients in which such treatment should be considered, and patients in which such treatment should be avoided. This also allows identification of patients in whom the risk of infection is increased. Such individuals may then be monitored more carefully and subjected to more rigorous checks and procedures in order to avoid such an infection occurring.

Ideally, the result of a method of the invention should be predictive of a specific outcome such as mortality, i.e. ideally the skilled person would like to be able to determine clinical outcome, for example survival or death, on the basis of such a method.

A receiver operating characteristic (ROC) curve may allow this to be achieved. Such curves explore the relationship between the sensitivity and specificity of a clinical test for a variety of different cut points, thus allowing the determination of an optimal cut point, i.e. it will be desirable to select a cut point above which, deleterious outcome of liver failure, such as increased infection risk, increased mortality and decreased responsiveness to immunotherapy is indicated and below which a more positive prognosis is indicated.

Commonly used measures of the performance of a clinical test are the sensitivity and specificity. Sensitivity is the probability that the disease (or outcome in the case of the present invention) is diagnosed when it is actually present and specificity is the probability that the disease is identified as being absent when it properly is absent. Ideally, both of sensitivity and specificity should be one. However, changing the cut point to try to increase one of sensitivity and specificity will usually result in a decrease in the other.

The ROC curve is a graphical technique for establishing the optimal cut point. In order to construct a ROC curve one needs to calculate the sensitivity and specificity for each possible cut point value. To make the ROC graph, the X-axis is 1 minus the specificity and the Y-axis is the sensitivity. A diagonal line is drawn from the lower left corner to the upper right corner. This graph reflects the characteristics of a test with no discriminating power. The closer the graph gets to the upper left corner the better it is at discriminating between cases and non-cases. An index of the goodness of the test is the area under the curve—the closer this value is to one the better the discriminating power of the test.

Accordingly, an ROC curve may be used to establish a cut point for an assay of the invention. A score above the cut point may be indicative of deleterious outcome, whereas a score below the cut point may be indicative of non-deleterious outcome.

The cut point can be selected depending on the requirements of the test, for example whether it is more important to exclude false positives or whether it is more important to identify all true positives. In the case of a test for identifying those patients admitted with liver failure who will die, it is important that all of the those patients are identified in which case the cut point may well also identify a number of false positives.

An appropriate cut point may be identified by those skilled in the art. As demonstrated in the Examples, using the Phagoburst® kit, a cut point of 55% resting burst has been shown to be a useful predictor when evaluating survival in patients with alcoholic cirrhosis and cirrhosis with alcoholic hepatitis. Such a cut off of resting burst 55% had a sensitivity of 75% and a specificity of 64% for predicting death. Using this test, a patient having less than 55% resting oxidative burst can be classified as having a lower risk of infection, lower mortality, and higher probability of response to immunosuppressive treatment such as steroid treatment. A patient having greater than or equal to 55% resting oxidative burst using this test can be classified as having an increased risk of infection, increased mortality, and decreased likelihood of response to immunosuppressive treatment such as steroid treatment.

The Examples also show that a cut off of 42% GMFI in the Phagotest® assay had a sensitivity of 86% and a specificity of 76% for predicting death. A patient having less than 42% of normal GMFI can be classified as having increased risk of infection, increased mortality and decreased likelihood of response to immunosuppressive treatment such as steroid treatment. A patient having greater than or equal to 42% of normal GMFI in this assay can be classified as having a decreased risk of infection, decreased mortality and increased likelihood of response to immunosuppressive treatment.

Alternatively, the method of the invention may be used to give relative or comparative prognostic information about an individual. For example, for some measures of neutrophil function a linear relationship may exist, with greater deviation from normal function correlating with increasing severity of liver disease or increasingly poor prognosis for the patient.

The method of the invention may be carried out in combination with one or more additional scoring systems used to assess the severity of liver disease and hepatic encephalopathy and also the prognosis of subjects. For example, from about two, three, four or more to about five, six, seven, eight or more scoring systems may be combined with those of the invention. Such additional scoring systems include the Child-Pugh, West Haven Criteria, Glasgow Coma Scale or modified Child-Pugh scoring system. Alternatively, or in addition, DF, SOFA, MELD or APACHE II may be used scoring system may be used. Points are assigned to parameters including serum bilirubin levels, serum albumin levels and to signs including presence of ascites or encephalopathy. Subjects to be treated may be classified in Child-Pugh class A, B or C. Generally subjects to be treated are classified in Child-Pugh class C.

The assessment of liver function may be useful in a wide range of situations. For example, the method allows the patients with liver dysfunction to be distinguished from those with no liver dysfunction. Thus, the progression of liver disease may be monitored using the method of the invention; in particular those patients who are likely to suffer from a deleterious outcome may be identified. That is to say, the method of the invention may be used to predict the outcome of liver disease and particularly liver failure.

Thus, the invention allows the selection of suitable treatment for an individual with liver disease. A patient who shows increased levels or activity of endotoxin or abnormal neutrophil function, for example increased neutrophil activation or decreased neutrophil phagocytosis as described herein, will be less likely to respond well to conventional treatments of liver disease, such as steroid treatment, antibiotic administration and immunosuppressive therapies. Indeed, it is likely that if immunosuppressive therapies were administered to such a patient, the prognosis of that patient would worsen, with an increased risk of infection and mortality. The present invention therefore allows the selection of a suitable approach for treatment of liver failure in an individual, depending on whether that individual also exhibits abnormal endotoxin levels or activity or neutrophil function. If the patient does not exhibit abnormal endotoxin levels or activity or neutrophil function, then immunotherapies, antibiotic administration or steroid treatment would be expected to be beneficial.

Liver failure is the final stage of liver disease. Liver failure is divided into types depending on the rapidity of onset. Acute liver failure develops rapidly, but chronic liver failure may take months or years to develop. By definition, liver failure occurs when the liver is so diseased, and functioning so poorly, that encephalopathy is evident. Any progressive liver disease can result in liver failure; examples include: acetaminophen toxicity, cirrhosis, viral hepatitis, and metastatic cancer of the liver. Other signs of liver disease such as jaundice, ascites, fetor hepaticus, and failure of coagulation indicate that the liver is having trouble performing its normal physiological duties, but it is not termed liver failure until the mental status changes appear.

The prognosis for patients with liver disease or liver failure is difficult to estimate because the condition has many causes. According to the invention, it is, however, possible to predict the clinical outcome of liver disease, in particular in patients with acute liver failure, as well as in those with ACLF. It is particularly useful in the prediction of clinical outcome in patients with alcoholic hepatitis.

Accordingly, the method of the invention may be carried out on an individual whose liver is decompensated or which shows hepatic encephalopathy. The individual's liver may be in the compensated state. The method is preferably carried out on an individual who is in liver failure. The individual may have chronic liver disease. The individual may have liver cirrhosis, for example with or without alcoholic hepatitis. The individual may have acute liver failure. The individual may have hepatic encephalopathy.

The onset of both acute and chronic liver disease may be due to a xenobiotic cause. For example, the individual may have been exposed to a chemical, drug or some other agent which causes liver damage. The individual may have a reaction to an over-the-counter, prescriptive or "recreational" drug which causes liver damage. The individual may have been taking Rezulin™ (troglitazone; Parke-Davis), Serzone™ (nefazodone; Bristol-Myers Squibb) or other drugs thought to cause liver damage. The individual may be one who has had an overdose of a particular drug or exceeded the recommended dosage of a drug capable of causing liver damage. For example, the individual may have taken an overdose of paracetamol. The individual may have been exposed to chemicals which can cause liver damage such as, for example, at their place of work. For example, the individual may have been exposed to such chemicals in an industrial or agricultural context. The individual may have consumed plants which contain compounds which can cause liver damage, in particular this may be the case where the individual is an animal, such as a herbivore. For example, the individual may have consumed a plant containing pyrrolizidine alkaloid such as ragwort. The individual may have been exposed to environmental toxins thought to cause liver disease.

Drug-related liver toxicity comprises more than 50% of all cases with acute liver disease (acute liver failure). Acetaminophen-(also known as paracetamol and N-acetyl-p-aminophenol) toxicity is the most common cause of acute liver failure in the United States and Great Britain. Long-term moderate to heavy alcohol users who take acetaminophen in therapeutic or modestly excessive doses are at risk of severe hepatic injury and possibly acute liver failure. Alcohol use potentiates the toxic effects of acetaminophen. Idiosyncratic drug toxicity also contributes to acute liver failure. Idiosyncratic drug toxicity is thought to be a hypersensitivity response wherein the individual responds to a drug in a pharmacologically abnormal way. This abnormal response can lead to acute liver failure.

The acute liver failure or chronic liver disease may be caused by infection with a pathogenic organism. For example, the liver disease may be due to viral infection. In particular, the individual may be infected, or have been infected, with a virus which causes hepatitis. The individual may have chronic viral hepatitis. The virus may, for example, be hepatitis B, C or D virus. In some cases, and in particular where the individual has viral hepatitis, the individual may also be infected with HIV-I or II. The individual may have AIDS. It is possible that the individual may have been, or be, infected with other organisms which cause liver disease and in particular those which are present in the liver during some stage of their life cycle. For example, the individual may have, or have had, liver fluke.

The individual may have an inherited disease which causes, or increases the risk of, chronic liver disease. For example, the individual may have one or more of hepatic hemochromatosis, Wilson's disease or a-1-antitrypsin deficiency. The individual may have an inherited disorder which causes some kind of structural or functional abnormality in the liver which increases the likelihood of liver fibrosis. The individual may be genetically predisposed to develop an autoimmune disorder which damages the liver and hence which can contribute to liver fibrosis.

The chronic liver disease may be alcohol-induced. A man or woman to be treated may be, or have been, an alcoholic. He or she may be, or have been, consuming on average 50 or more units of alcohol per week, 60 or more units of alcohol per week, 75 or more units of alcohol per week and even 100 or more units of alcohol per week. The man or woman may be, or have been, consuming on average up to 100 units of alcohol per week, up to 150 units of alcohol per week and even up to 200 units of alcohol per week. The measurement of one unit of alcohol differs from country to country. Here, one unit equals 8 grams of ethanol in accordance with the United Kingdom standard.

The man or woman may have been consuming such levels of alcohol for 5 or more years, 10 or more years, 15 or more years or 20 or more years. The individual may have been consuming such levels of alcohol for up to 10 years, up to 20 years, up to 30 years and even up to 40 years. In cases of alcohol-induced liver cirrhosis the individual may be aged, for example, 25 years or over, 35 years or over, 45 years or over and even over 60 years.

The individual may be male or female. Women may be more susceptible to the adverse effects of alcohol than men. Women can develop alcoholic chronic liver disease in a shorter time frame and from smaller amounts of alcohol than men. There seems to be no single factor to account for increased susceptibility to alcoholic liver damage in females, but the effect of hormones on the metabolism of alcohol may play an important role.

Thus, the individual may be suffering from alcoholic hepatitis. Alcoholic hepatitis may range from a mild hepatitis, with abnormal laboratory tests being the only indication of disease, to severe liver dysfunction with complications such as jaundice (yellow skin caused by bilirubin retention), hepatic encephalopathy, ascites, bleeding esophageal varices, abnormal blood clotting and coma.

In the invention, the individual may have one or more of a number of other conditions known to result in liver damage such as, for example, primary biliary cirrhosis, autoimmune chronic active hepatitis, and/or schistosomiasis (parasitic infection). The individual may have or have had a bile duct blockage. In some cases, the underlying cause of liver disease may not be known. For example the individual may have been diagnosed as having cryptogenic cirrhosis. Accordingly, the individual may be suspected of having any of the conditions listed herein.

Methods for diagnosing liver disease such as acute liver failure and hepatic encephalopathy are well known in the art and in particular to clinicians and veterinarians in the field. Preferably, the individual will have been diagnosed as having liver failure, for example by a medical or veterinarian professional. The individual may display one or more symptoms associated with liver disease such as one or more of jaundice, ascites, skin changes, fluid retention, nail changes, easy bruising, nose bleeds, oesophageal varices, and in male individuals may have enlargement of breasts. The individual may display exhaustion, fatigue, loss of appetite, nausea, weakness and/or weight loss. The individual may also display one or more symptoms associated with hepatic encephalopathy such as one or more of confusion, disorientation, dementia, stupor, coma, cerebral edema, multiorgan failure (respiratory failure, cardiovascular failure or kidney failure), muscle stiffness/rigidity, seizures or speech impairment. The individual to be treated may or may not be taking other drugs to treat liver disease. The individual to be treated may be at risk of developing hepatic encephalopathy.

The liver disease may have been, or be, confirmed by physical examination including techniques such as ultrasound. Liver biopsies may have been taken to look for build up of fibrosis, necrotic cells, cellular degeneration and/or inflammation and other characteristic features of liver disease. Liver function may have been assessed in the individual to determine whether this is compromised in the individual. The nature and underlying cause of the liver disease may be characterized. Any history of exposure to causative agents of liver disease may be determined.

The individual to be treated may be at risk for hepatic encephalopathic episodes, for example patients who are awaiting liver transplants, surgical and/or portal hypertension patients. A person at risk for hepatic encephalopathic episodes is a person who has not suffered any hepatic encephalopathic episodes or has not suffered any hepatic encephalopathic episode for an extended period of time (about 12 weeks or longer), but has a disorder or medical condition which creates a risk of hepatic encephalopathic episodes. A hepatic encephalopathic episode is a clinical condition characterised by the presence of cerebral dysfunction in patients with liver disease or dysfunction. There is a wide spectrum of mental disturbances in hepatic encephalopathy which range from minimal where the main effects are a reduction in the quality of life, to overt which leads to coma and ultimately death.

In the invention, endotoxin in an individual is detected. Typically, the method is carried out in vitro or ex vivo on a sample from the individual. Where the method involves direct detection of endotoxin or endotoxin activity, the sample will typically be from a tissue or fluid that would be expected to comprise endotoxin. Where the method involves detection of a downstream effect of endotoxin, the sample will typically be from a tissue or fluid in which that effect would be expected. Where the method involves assessment of neutrophil function, the sample will generally be from a tissue known to contain neutrophils or a tissue which has been in contact with neutrophils.

The sample typically comprises a body fluid of the individual. The sample may be a sample of blood from the individual, such as a sample of blood, which comprises neutrophils. The sample may be a blood sample which has been processed to remove other components but to leave some components, for example neutrophils, present. For example, the sample may be a blood sample which has been fractionated and a fraction comprising neutrophils selected. Neutrophil function may be assessed in a population of neutrophils or in individual neutrophils. For example, some assays will measure the proportion of neutrophils in a sample having a particular characteristic or response. Other assays will assess the characteristics or function of individual neutrophils. The sample may be a component of blood which the neutrophil has been in contact with. The sample may contain neutrophils. The sample may not contain neutrophils. The sample my not contain cells. For example, the sample may be a plasma sample from an individual. Such samples may be obtained in any appropriate way. Methods for obtaining blood, plasma and other blood fractions are well known to those skilled in the art.

The invention also provides a test kit for predicting the outcome of liver failure in an individual, which test kit comprises means for detecting endotoxin in the individual. These may be any means for carrying out a method as described herein. For example, the kit may comprise means for detecting the presence and/or amount of endotoxin or for detecting the presence and/or amount of a downstream effect of endotoxin. For example, in one embodiment, the kit may comprise means for determining the level of neutrophil function in the individual. Such a kit may comprise a sample of neutrophils and means for determining whether neutrophils are activated.

A test kit of the invention may optionally comprise appropriate buffer(s), enzymes, for example a thermostable polymerase such as Taq polymerase and/or control polynucleotides. A kit of the invention may also comprise appropriate packaging and instructions for use in a method for predicting the outcome of liver disease in an individual.

A test kit of the invention may also comprise an agent useful in the treatment of liver disease. Suitable agents for including in such a kit are agents as described herein.

The invention provides a method of treatment of liver failure, which method comprises detecting endotoxin in an individual by a method as described herein and thereby determining the prognosis of the individual. As explained herein, an abnormal endotoxin level such as increased endotoxin, increased endotoxin activity, increased neutrophil activation or decreased phagocytosis is indicative of a poor prognosis, with an increased likelihood of factors such as infection, organ failure and mortality, and a decreased likelihood that the individual will respond positively to some forms of treatment, such as steroid treatment, antibiotic treatment and immunosuppressive treatment. The method of treatment further comprises administering to the individual a therapeutically effective amount of an agent useful in the treatment of liver failure.

Thus, an agent which is useful in the treatment of liver failure may be for use in the treatment of liver failure in an individual, wherein the individual has increased endotoxin, endotoxin activity, or a downstream effect of endotoxin as described herein. For example, the individual may have been identified as having a poor prognosis using a method as described herein. The invention also provides use of an agent which is useful in the treatment of liver failure in the manufacture of a medicament for use in a method of treatment of liver failure in an individual, wherein the individual has been identified or is identifiable as having a poor prognosis using the method set out above.

The information obtained by assessing endotoxin (e.g. neutrophil function) can be used to select a suitable therapeutic agent. For example, if the endotoxin assessment leads to a classification of the individual as high risk as described herein, treatments such as immunosuppressives, steroids and antibiotics may be avoided. If the endotoxin assessment leads to a classification of the individual as low risk as described herein, treatments such as immunosuppressives, steroids and antibiotics may be selected for the treatment of that individual. Some agents may be suitable for administration direct to the individual, other agents may be used ex vivo, for example on a sample of blood or plasma from the individual. A suitable administration protocol may be determined by a clinician depending on the agent to be used.

The invention therefore also provides a method of treatment of liver failure, which method comprises determining whether or not the individual has abnormal endotoxin using a method as described above and (a) if the individual does have abnormal endotoxin (e.g. abnormal neutrophil function), administering to the individual a therapeutically effective amount of an agent useful in the treatment of liver failure which does not have an immunosuppressive effect; or (b) if the individual does not have abnormal endotoxin (e.g. neutrophil function), administering to the individual a therapeutically effective amount of an agent useful in the treatment of liver failure which does have an immunosuppressive effect.

The invention also provides the use of an agent which is useful in the treatment of liver failure, which agent does not have an immunosuppressive effect, in the manufacture of a medicament for use in a method of treatment of liver failure in an individual, wherein the individual has been identified as having abnormal endotoxin and/or abnormal neutrophil function and/or poor prognosis using the method set out above.

Similarly, the invention provides the use of an agent which is useful in the treatment of liver failure, which agent does have an immunosuppressive function, in the manufacture of a medicament for use in a method of treatment of liver failure in an individual, wherein the individual has been identified as not having abnormal endotoxin and/or neutrophil function using the methods set out above.

In a further aspect, the invention provides particular methods and uses for the treatment of liver disease.

As explained above, the Inventors have demonstrated that the transmissible activity of the humoral factor linked to disease prognosis is removable by endotoxin removal. Accordingly, the treatment of liver failure in the methods and uses described herein may be treatment to remove, or reduce the level of endotoxin in the individual. For example, an individual having abnormal endotoxin as defined herein may be treated in such a way as to reduce the level of endotoxin circulating in the blood of the individual.

This may be achieved by numerous methods known in the art. For example, endotoxin levels may be reduced by administering to the patient a therapeutically effective amount of an agent which reduces endotoxin levels. This agent may bind directly to endotoxin thereby reducing its activity: it may bind to endotoxin and allow its clearance from the blood, or it may otherwise effect the structure and/or activity of endotoxin in the blood. It is known in the art, for example, that endotoxin levels may be reduced by administering an anti-endotoxin antibody. Other agents, such as LPS binding protein or albumin may also be administered to reduce the level of circulating endotoxin. Similarly, substances which neutralise the activity of endotoxin, such as LPS-neutralising CD-14 antibodies may be used to reduce circulating endotoxin levels.

Alternatively, endotoxin may be removed directly from the circulation. For example, blood or plasma may be treated to directly remove endotoxin ex vivo. For example, plasma may be passed through an endotoxin removal column such as a column comprising a substance which binds endotoxin. Suitable substances are known in the art and include Polymyxin B and polyethyleneimine.

Various approaches for removing endotoxin from a sample have been described in the art. For example, EP-A-0 129 786 describes the use of Polymyxin B covalently immobilized on polystyrene fibres for the removal of endotoxins from blood. Falkenhagen et al (Artificial Organs (1996) 20:420) describes the removal of endotoxin from plasma using polyethyleneimine coated beads. WO 01/23413 describes oligopeptides having a high degree of dispersity which are used to selectively remove endotoxin from blood or plasma. U.S. Pat. No. 5,476,715 describes materials for the removal of endotoxin from a sample, which comprise a porous carrier made from polymers of acrylic acid and methacrylic acid with a particular particle size and spacing. Staubach et al (Transfusion and Apheresis Science (2003) 29: 93-98) describes a device for endotoxin adsorption which is based on immobilized albumin. There are thus a number of available methods which could be used to remove endotoxin from a sample. Any of these methods may be used or adapted for use in accordance with the present invention. The skilled reader would be able to select a suitable method and conditions for its use.

A method may be carried out ex vivo for the treatment of blood from an individual having liver failure to remove endotoxin. For example, this may be a method of treating blood extracorporeally by selectively removing endotoxin from the blood. This may be used to alter the function of neutrophils in the blood where those neutrophils have abnormal function as described herein. Blood which has been treated in this way may be returned to the individual for therapeutic purposes, or may be used for another purpose. For example, blood may be treated in this way prior to transfusion into a different individual.

Selective removal of endotoxin requires that endotoxin is removed in preference to other components of the blood. Other blood components may be removed in smaller quantities, but the predominant component being removed should endotoxin. Optionally, other blood components which have been removed with the endotoxin may be subsequently returned to the blood.

Accordingly, the invention provides a method of treatment of liver failure, which method comprises administering to the individual a therapeutically effective amount of an agent which reduces the level of circulating endotoxin, or the level of circulating endotoxin activity in the bloodstream of the individual. Alternatively, a method of treatment of liver failure may comprise the step of removing endotoxin from the blood or plasma of an individual suffering liver failure. As explained above, the individual may be an individual that has been identified or an individual that is identifiable as having a poor prognosis using a method as described herein. For example, the individual may have increased endotoxin levels, increased endotoxin activity or abnormal neutrophil function such as increased neutrophil activation or decreased phagocytosis.

The invention also provides use of an agent which reduces the level of circulating endotoxin in an individual in the manufacture of a medicament for use in the treatment of liver failure in that individual.

Thus, the condition of an individual having liver failure may be improved by administration of an agent which is used in the treatment of liver disease. A therapeutically effective amount of an agent which is used in the treatment of liver disease may be given to an individual identified or identifiable according to a method of the invention.

An agent which is used in the treatment of liver disease may be administered in a variety of dosage forms. Thus, an agent may be administered orally, for example as tablets, troches, lozenges, aqueous or oily suspensions, dispersible powders or granules. The agent which is used to treat disease may also be administered parenterally, either subcutaneously, intravenously, intramuscularly, intrasternally, transdermally or by infusion techniques. The agent may also be administered in the form of a suppository. A physician will be able to determine the required route of administration for each particular patient.

The formulation of an agent used in the treatment of liver disease will depend upon factors such as the nature of the exact agent, whether a pharmaceutical or veterinary use is intended, etc. An agent which is to be used to treat liver disease may be formulated for simultaneous, separate or sequential use.

An agent used in the treatment of liver disease is typically formulated for administration in the present invention with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

A therapeutically effective amount of an agent used in the treatment of liver disease may be administered to a patient identified or identifiable as having liver disease or a poor prognosis in such liver disease using the method of the invention. The dose of an agent which used in the treatment of liver disease may be determined according to various parameters, especially according to the substance used; the age, weight and condition of the patient to be treated; the route of administration; and the required regimen.

Again, a physician will be able to determine the required route of administration and dosage for any particular patient. A typical daily dose is from about 0.1 to 50 mg per kg of body weight, according to the activity of the specific inhibitor, the age, weight and conditions of the individual to be treated, the type and severity of the degeneration and the frequency and route of administration. Preferably, daily dosage levels are from 5 mg to 2 g.

A suitable agent may be used in the manufacture of a medicament for use in a method of treatment of liver disease in an individual, wherein the individual has been identified as having abnormal endotoxin such as abnormal neutrophil function according to the method of the invention as described above.

Thus, a method for the treatment of liver disease in an individual may comprise: (i) determining whether the individual has abnormal endotoxin such as abnormal neutrophil function using a method of the invention as described above; and (ii) administering to an individual identified in (i) as having abnormal neutrophil function, a therapeutically effective amount of an agent as disclosed above, particularly an agent which reduces the amount or activity of endotoxin.

Products containing means for predicting the outcome of liver disease in an individual and an agent which may used in the treatment of liver as a combined preparation for simultaneous, separate or sequential use in a method of treatment of the human or animal body by therapy. Thus, such products may comprise both means for diagnosis and means for therapy.

All publications and patent applications mentioned in this specification are indicative of the level of those skilled in the art to which this invention pertains.

All publications and patent applications are herein incorporated by reference to the same extent as if each individual publication or patent application was specifically and individually to be incorporated by reference.

Although the foregoing invention has been described in some detail by way of illustration and example for purposes of understanding, it will be clear to those skilled in the art that certain changes and modifications may be practiced within the scope of the appended claims.

The following Examples illustrate the invention:

EXAMPLES

Methods:
Patient Selection

All patients or their relatives gave written informed consent and the study was approved by the local ethics committee. Patients admitted with evidence of alcoholic cirrhosis were screened for this study, at the time of a clinically indicated transjugular liver biopsy. The patients were included if they were admitted with acute decompensation of alcoholic cirrhosis manifested by increasing jaundice, ascites or hepatic encephalopathy grade 1 or 2 and there was no if there was microbiological evidence (routine cultures of urine, blood, sputum and ascites) of infection. Patients were excluded if they were <18 or >75 years, had evidence of: organ failure (inotrope requirement, renal failure—creatinine>150, hepatic encephalopathy grade 3 or 4, need for mechanical ventilation, severe cardiac dysfunction), hyponatremia, hepatic/extra-hepatic malignancy, within 3 days of gastrointestinal bleeding or if they received any immunomodulatory therapy prior to entry in the study.

Study Design

Following correction of any associated electrolyte disturbance or hypovolemia, blood samples were collected and used for routine biochemistry, neutrophil function, cytokine profile and thiobarbituric acid (T-BARS/modified MDA) detection. Peripheral venous blood was aseptically collected into pyrogen free tubes (BD Vacutainer™ Lithium-Heparin, 60 U per tube, Beckton and Dickinson, Plymouth, UK)) from patients and healthy volunteers. For experiments with cells, blood was kept at room temperature, for harvesting plasma, blood was placed on ice immediately. After centrifugation the plasma was aliquoted under pyrogen-free conditions into endotoxin-free cryotubes (Corning Inc., Corning, N.Y.) and stored at −80° C. until further analysis. 100 μL of whole blood or 50 μL of isolated neutrophils and 50 μL of plasma were used to perform the Phagoburst® or the Phagotest®. For all experiments strict precautions were taken to avoid endotoxin contamination by working aseptically and using endotoxin-free equipment. Bilirubin, albumin, liver function tests, coagulation parameter, full blood count, and C-reactive protein (CRP) were routinely assessed. Maddrey's discriminant function and Pugh score were calculated. The patients were followed prospectively over a period of 90 days. The occurrence of organ dysfunction and mortality were recorded. Screening blood cultures were performed regularly, and our unit policy was to use prophylactic antibiotics at the time of presentation in most patients.

Neutrophils

Neutrophils were either investigated in a whole blood assay (as described below) or after isolation by a one-step gradient centrifugation.

Figure 1:
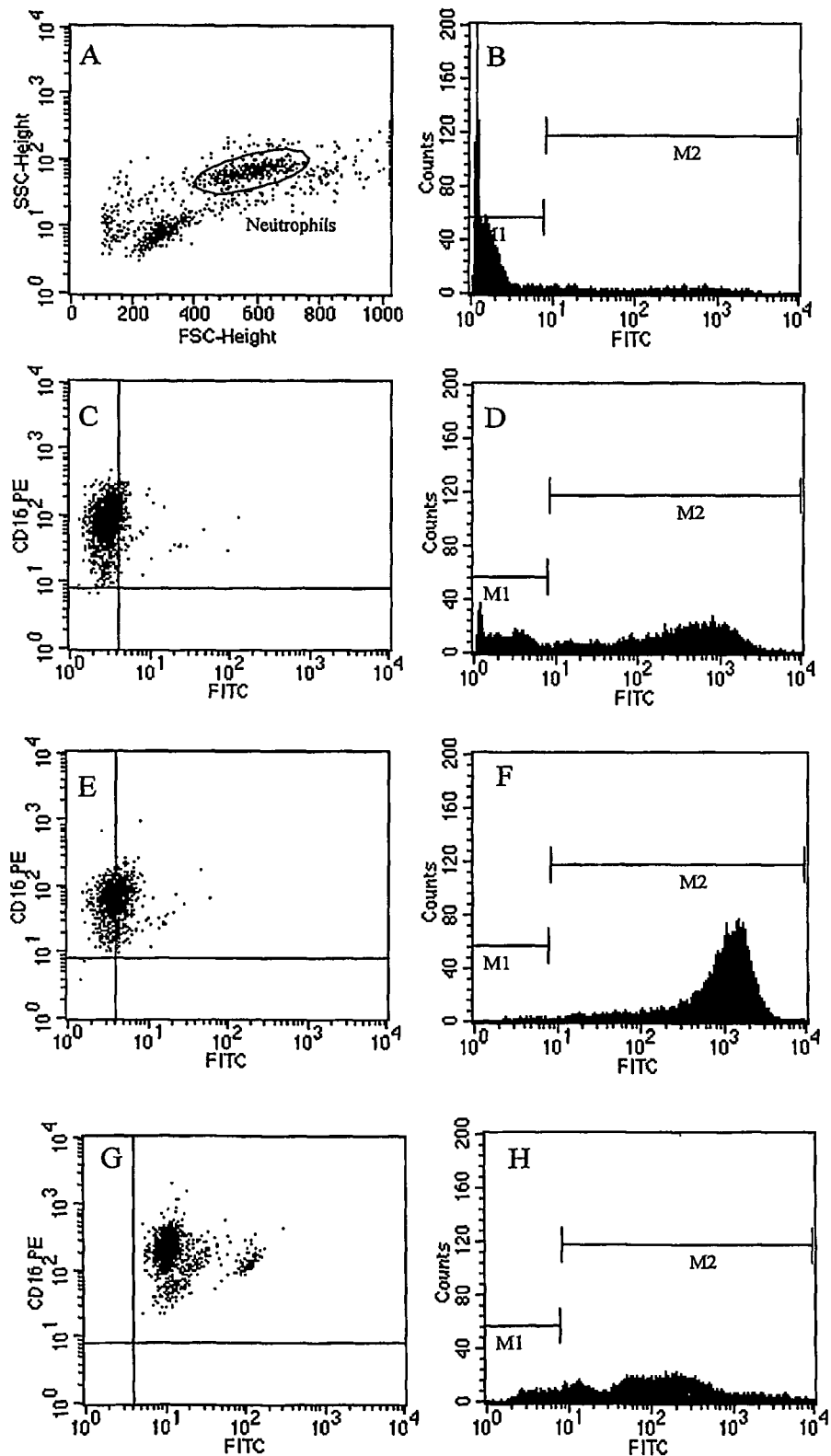
FIG. 1: Representative FACS-analysis plots for Phagotest® and Bursttest®. (A) Neutrophils were gated according to their forward and side scatter characteristics. (B) Analysis of phagocytosis: On a sample without bacteria markers are set that more than 99% of the gated neutrophils are within the first maker. (C) Representative FACS-plot from a patient with high resting oxidative burst. The percentage of double positive (CD 16 positive cells producing reactive oxygen metabolites determined by green fluorescence in FL-1) is measured. (D) Corresponding FACS-plot of a patient with very low geometric mean of fluorescence intensity (GMFI) (E) Representative FACS-plot from a patient with low resting oxidative burst, (F) Corresponding FACS-plot of a patient with low GMFI, (G) Representative FACS-plot from a healthy control subject, (H) Corresponding FACS-plot of a healthy control with normal GMFI
Figure 2:
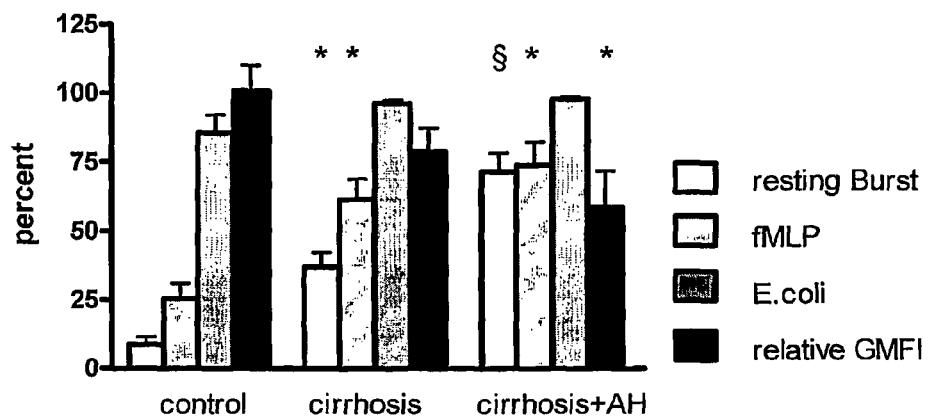
FIG. 2: Resting oxidative burst, oxidative burst after stimulation with fMLP or E. coli and relative GMFI for controls, patients with alcoholic cirrhosis and cirrhosis+AH. * significant versus control. §significant versus control and cirrhosis.
Figure 3:
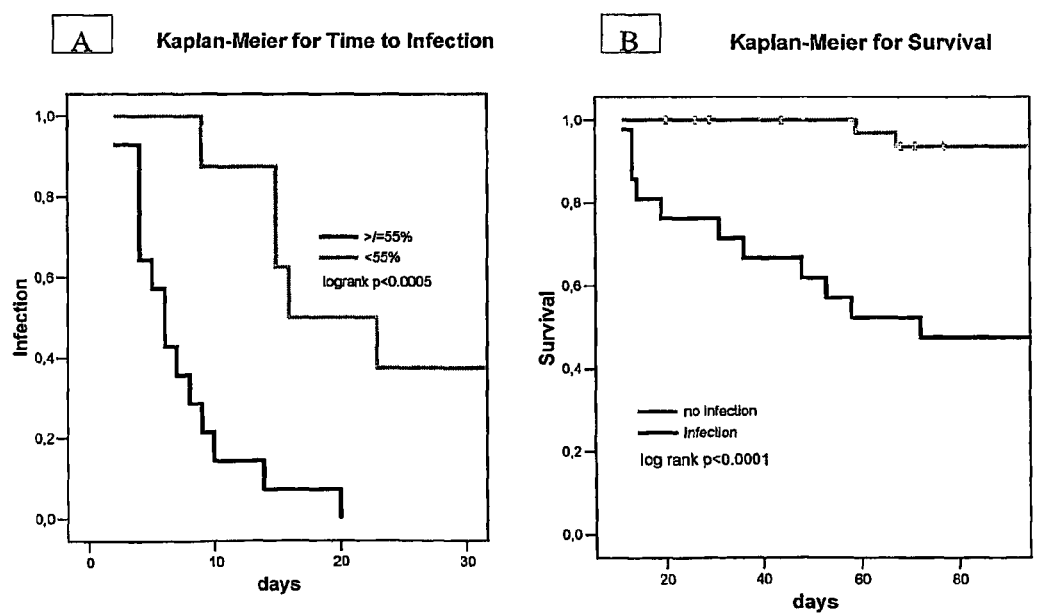
FIG. 3: (A) Analysis for time to infection (Kaplan-Meier) for patients with high versus low resting burst. (B) Kaplan Meier survival curve and log-rank analysis for patients with and without culture positive infection.

Neutrophil Activation (Oxidative Burst) and Phagocytosis:

The Phagoburst® kit (Orpegen Pharma, Heidelberg, Germany) was used to determine the percentage of neutrophils that produce reactive oxidants by stimulation with opsonized *E. coli* bacteria or without any stimulus according to the manufacturers instructions. The Phagotest® (Orpegen Pharma, Heidelberg, Germany) was used to measure the overall percentage of neutrophils showing phagocytosis and the individual cellular phagocytotic activity using FITC-labelled opsonized *E. coli* bacteria (see appendix). Neutrophils were gated on forward and side scatter (FIG. 2A) characteristics and subsequently the percentage of CD16 positive cells—FITC positive cells, corresponding to the percentage of neutrophils undergoing phagocytosis and the geometric mean of fluorescence intensity (GMFI), corresponding to the number of bacteria engulfed by one cell, was analyzed (FIGS. 1B, D, F). To avoid variability due to batch-to-batch difference of bacteria, results were normalized to the mean of at least 3 healthy control samples for each new batch of bacteria used. Samples were analyzed in triplicate or duplicate.

Incubation with Endotoxin

Endotoxin (*E. coli* 0111:B4 Lot 085K4068, Sigma Aldrich, St. Louis, Mo., USA) was prepared as a stock solution of 1 mg/ml and freshly diluted with PBS to the concentrations indicated. Whole blood was incubated for 1 h with the respective endotoxin concentration at 37° C. in a water bath before Phagotest® or Bursttest® were performed.

Endotoxin Removal from Patient's Columns

Using Detoxigel:

Detoxi-Gel® Affinity-pack prepacked columns (Pierce Biotechnology, Rockford, Ill.) containing an endotoxin removal gel consisting of immobilised polymixin B that binds to the lipid A portion of bacterial lipopolysaccharide were used to remove endotoxin from plasma samples. 100 µL of this endotoxin-free, diluted plasma sample were incubated with 504 of cell suspension and Bursttest® or Phagotest® was performed as indicated.

Using CD14 Antibody:

100 µL of plasma and 50 µl of PBS were incubated with 5 µL of an anti-human CD14 antibody (Clone 11D18, Immuntools, Friesoythe, Germany) (known to neutralise LPS) for 60 minutes before performing the Phagotest® or the Bursttest®.

Cytokines

Plasma TNFα, sTNFαR1, sTNFαR2, IL-6 and IL-8 were determined using commercially available kits (BioSource International, Nivelles, Belgium).

Malondialdehyde and Prostaglandin F2α

Malondialdehyde (MDA) was determined using a modified thiobarbituric acid reactive substances assay as known in the art. Free 8-Isoprostane F2alpha was assayed with a commercial EIA kit (Cayman Chemical, Ann Arbor, Mich.).

Statistics

For comparison of two groups Chi-Square test, t-test or Mann-Whitney test were used as appropriate, for comparison of more than two groups ANOVA test with Turkey's (equal variances) or Dunnett C (no equal variances) post hoc analysis for data sets was used as appropriate. To assess diagnostic accuracy, receiver operating characteristic (ROC) curves were constructed and areas under the curve (AUROC) were calculated. Differences in survival were analysed by the log rank test. Pearson's correlation coefficient was used to assess relationship between variables. Results are given as mean±SEM. A p<0.05 was considered as significant Myeloperoxidase Activity A group of 10 patients was selected with varying severity of liver disease. Neutrophil resting burst (%) was measured in a sample from each patient as described herein. Plasma (cell free) myeloperoxidase (MPO) activity was also assessed.

Blood was collected into pre-cooled EDTA (as an anticoagulant) coated tubes and stored on ice. The samples were then centrifuged at 3000 rpm for 10 minutes at 4° C. to separate cellular components, and the resulting plasma collected and stored in sterile cryovials at −80° C. until analysis.

Analysis comprised incubation of plasma (50 µL) in a solution of 100 mM phosphate buffer (pH 7), containing 13 mM guaiacaol (2-methoxyphenol) and 0.02% cetyltrimethylammoniumbromide (CTAB) at 37° C. (total volume 1 mL). Following an equilibration period of 5 minutes the reaction was started with the addition of 1 µmole hydrogen peroxide ($H_2O_2$). The progress of the reaction was monitored at 470 nm for 60 minutes in a diode array spectrophotometer. The activity of MPO was determined from the rate of change in absorbance at 470 nm (after removal of background absorbance signals), and expressed in guaiacol units (defined as the amount of enzyme that forms 1 µmmole tetraguaiacol per minute, using an extinction coefficient of 26 $mM^{-1}cm^{-1}$).

This method is adapted from: Cramer et al J Immunol Methods. 1984 May 11; 70(1):119-25.

Results

Patient Characteristics

Of the 72 patients screened, 63 patients were included. Patients were classified histologically into those having significant inflammation, using a modified NASH scoring system (cirrhosis+AH) as compared to cirrhosis alone. Patients with cirrhosis+AH (n=23) were more severely ill as evidenced by a higher MELD and Pugh score (p<0.001) as compared to patients with cirrhosis alone (n=40). Patients with cirrhosis+AH also had significantly higher CRP (p<0.005), white blood cells (p<0.001), bilirubin (p<0.001) and prothrombin time (p<0.001). Patients had higher levels of TNFα, IL6, IL8, sTNFαR1, sTNFαR2, MDA and prostaglandin F2α than controls. Patients with cirrhosis+AH had significantly higher levels of ILL, IL8 and sTNFαR2, but no statistically significant changes were noted for TNFα, sTNFαR1 and oxidative stress. No correlation with disease severity was found. For the ex vivo experiments blood or plasma from 16 of these 63 patients was used. The baseline clinical data for these 63 patients were not significantly different from the whole cohort. Table 1 shows the baseline characteristics for all patients and for the subgroups having high and low resting bust (see below).

Oxidative Burst and Phagocytosis in Patients with Alcoholic Cirrhosis

In un-stimulated patient neutrophils, neutrophil oxidative burst was increased when compared with controls. Neutrophils from patients with alcoholic cirrhosis overall had a 5.6 times higher resting oxidative burst (p<0.001) than healthy controls. Neutrophils from patients with cirrhosis+AH had significantly higher resting oxidative burst compared to patients with cirrhosis alone (p<0.001) or controls (p<0.001, FIG. 2A). Stimulation with fMLP, indicating priming, caused a significant higher oxidative burst reaction in patients with cirrhosis (p=0.01) and cirrhosis+AH (p=0.001) as compared to controls whereas there was no difference in response to PMA between the groups. The difference between resting burst and fMLP response was significantly lower in patients with cirrhosis+AH (1.8±4.7) than in patients in cirrhosis (22.4±6.9, p=0.02), showing that addition of fMLP in patients with cirrhosis+AH is not able to enhance function of the cells any more. Furthermore, following stimulation with *E. coli*, the relative increase in oxidative burst from resting levels was significantly diminished in cirrhosis+AH patients compared with cirrhosis alone (p=0.001) or controls (p<0.001, FIG.

2B). Phagocytotic capacity was measured by the geometric mean of fluorescence intensity (GMFI), which indicates the number of bacteria engulfed by one cell. Patients with cirrhosis+AH engulfed significantly less bacteria than controls (p=0.031, FIG. 2C). The percentage of cells engulfing at least one bacterium did not differ between the groups.

Figure 4:
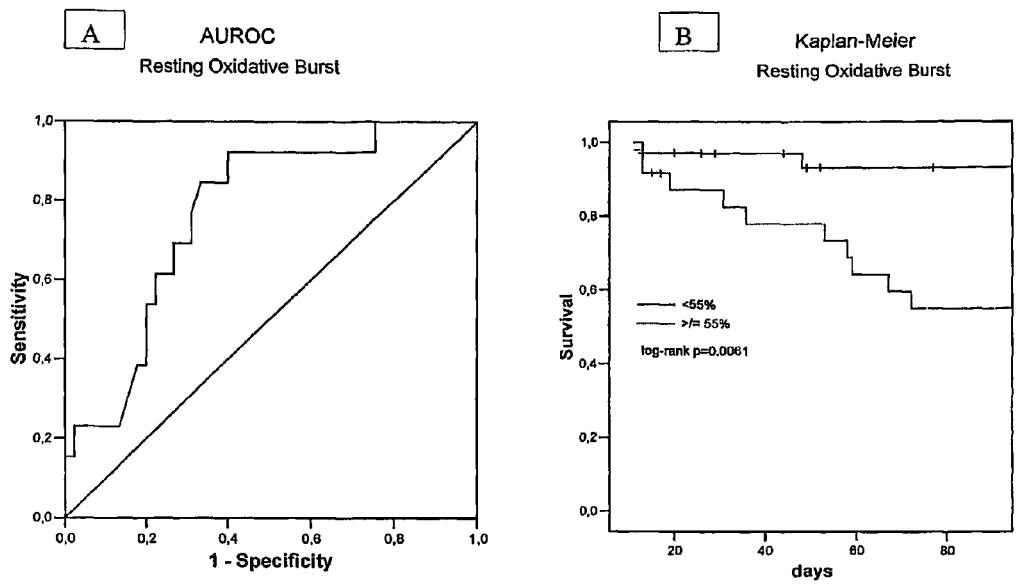
FIG. 4: (A) Area under the receiver operating curve to determine the predictive utility of measurement of oxidative burst in determining survival. A cutoff of resting burst<55% had a sensitivity of 75% and a specificity of 64% for predicting death. Area=0.77; Std. Error=0.07; significance=0.003; cut-off=55; sensitivity=0.77; specificity=0.69. (B) Kaplan Meier survival curve and log-rank analysis for patients stratified for high (>/=55%) or low (<55%) resting oxidative burst.

Association of Resting Oxidative Burst and Phagocytosis with Infection, Organ Failure and Survival Seventeen (26%) developed organ failure and 13 (21% of all studied patients) died during index hospital admission. The most common organ failure encountered was renal, noted in 15 of the patients with organ failure (88%), with 4 patients developing this as part of multi-organ failure with requirement for ventilation and circulatory support. By 90 days, 14 (22%) patients had died, 47 were alive and 2 were lost to follow-up. Resting oxidative burst was found to be predictive of 90-day survival (AUROC 0.77, p=0.003, FIG. 4A) and organ failure (AUROC 0.76, p<0.001). A cutoff of resting burst<55% had a sensitivity of 77% and a specificity of 69% for predicting death. Patients with a resting oxidative burst<55% survive significantly better than those with a resting burst>/=55% (p<0.005, FIG. 4B). Phagocytic function was also predictive of survival (AUROC 0.80, p=0.02, FIG. 5A) and organ failure (AUROC 0.91, p<0.0001). A GMFI of lower than 42% of normal within the studied patient population had a sensitivity of 86% and a specificity of 76% to predict mortality (FIG. 5B).

In 42 (66%) patients infection was clinically suspected during the course of the hospital admission although none of the patients included had a proven infection at the time the neutrophil function was assessed. These data should be considered in context since our protocol for management, necessitates the use of broad spectrum antibiotics as soon as an infection is suspected. In 26 of these patients (62%), culture positive infection was verified. In 13, more than one organism was found. Patients with a high resting burst (>55%) were more likely to develop culture positive infections (57% versus 27%, chi-square p=0.01), earlier during hospital stay (8 vs 23 days, p=0.04) and with more than one organism (n=10; n=3 in patients with low resting burst). Patients with cirrhosis+AH were more likely to develop culture positive infections (65% versus 28%, p=0.004). Those patients who developed culture positive infections, were more likely to develop organ failure (p=0.001) and to die (p=0.002). 67% of patients with a GMFI below 42% developed culture positive infection, whereas only 21% of patients with a GMFI above 42% (p=0.007) did so. Patients with low GMFI developed infections earlier during their hospital stay (9 vs 47 days, p=0.03)

Effect of Patients Plasma and Normal Plasma on Neutrophils Oxidative Burst

Plasma from patients with a high resting burst (>55%; n=6) induced a high resting burst in normal neutrophils (p=0.005) whereas plasma of patients with a low resting burst (<55%; n=6) failed to do so (FIG. 6). The burst-inducing effect was detectable immediately after mixing plasma and cells but could also be shown after up to one hour of incubation (results not shown). This result indicated that there is a transmissible factor present in patient's plasma which causes neutrophils activation.

When isolated neutrophils of patients with high resting burst in the whole blood assay were incubated with normal plasma, the resting burst decreased significantly as compared to isolated neutrophils incubated with the patients own plasma (p=0.02; FIG. 7). These experiments suggested that the removal of a factor present in plasma was able to reduce the high resting burst in patients' cells.

Effect of Patients' Plasma and Normal Plasma on Phagocytosis

Normal neutrophils incubated with plasma from patients with a low resting burst did not differ from control, whereas normal neutrophils incubated with plasma from patients with high resting burst showed a 22% decrease in GMFI (p=0.03, n=6) (FIG. 8). Patients neutrophils incubated for 60 minutes with normal plasma showed a 22% increase (p=0.03, n=6) in phagocytosis as compared to patients neutrophils incubated with their own plasma. These results indicate that impairment of phagocytic function may be due to a serum factor that is transmissible and reversible.

Effect of Endotoxin on Oxidative Burst and Phagocytosis

Blood from five healthy volunteers was incubated with rising concentrations of endotoxin. There was a dose dependent increase in resting burst (p<0.0001, one way ANOVA with Turkey post hoc analysis; FIG. 9). By incubation of patient's neutrophils with endotoxin, the relative GMFI was reduced by 20% (n=8, p=0.02, FIG. 10). These results indicate that endotoxin activates normal neutrophils in a dose-dependent manner thereby mimicking the effect seen by incubation with patients' plasma.

Effect of Removing Endotoxin from Patients Plasma

Using Detoxi-Gel Columns:

Plasma from patients shown to have a high resting burst in the whole blood assay was able to induce a high resting burst in normal neutrophils. Endotoxin free plasma (obtained from passage through the columns) did not induce a high resting burst in normal neutrophils (p<0.001, n=9). Plasma from patients with low resting burst (p=0.91, n=4) and normal plasma (p=0.25, n=3) did not change resting burst. (FIG. 11) Endotoxin removal from the plasma of patients with a high resting burst (n=11) increased GMFI by 31% (p=0.03) as compared to cells incubated with untreated plasma. Plasma from patients with low resting burst (p=0.16, n=8) and normal plasma (p=0.85, n=5) that was passed over the column did cause any changes in GMFI (FIG. 12). This set of experiments shows that endotoxin removal by polymixin B reverses the burst-inducing and phagocytosis-decreasing effect of patients' plasma.

Using LPS-neutralising Antibodies:

Incubation with a LPS neutralising anti-human CD14 antibody prevented the induction of high burst in normal cells by plasma from patients with a high burst (p<0.001, n=7). Incubation of plasma from patients with low burst (p=0.733, n=8) or normal plasma (p=0.25, n=3) with the antibody did not change burst (FIG. 11). Incubation of plasma from patients with a high burst with a LPS neutralising anti-human CD14 antibody increases GMFI by 20% (p=0.04, n=11) whereas this antibody does not cause any changes in GMFI when plasma from patients with low burst (p=0.17, n=8) or normal plasma (p=0.78, n=3) was used (FIG. 12). This finding underpins the observation that endotoxin may be responsible for the induction of high resting burst in neutrophils.

Myeloperoxidase Activity

A comparison of neutrophil resting burst (%) and plasma (cell free) myeloperoxidase (MPO) activity showed a significant relationship (FIG. 13). This indicates that there is a strong link between the measured resting neutrophil activity and the amount of MPO released into the plasma. As MPO could be considered deleterious to normal metabolic function, when released from the controlled environment of the neutrophil, this finding may indicate a mechanism of damage occurring within liver disease. This data also indicates that plasma MPO activity may provide a useful measure of disease severity.

Methodology

Neutrophil Activation (Oxidative Burst) and Phagocytosis

The Phagoburst® kit (Orpegen Pharma, Heidelberg, Germany) was used to determine the percentage of neutrophils that produce reactive oxidants by stimulation with opsonized E. coli bacteria or without any stimulus according to the manufacturers instructions. In brief, 100 µl of heparinized whole blood or isolated neutrophils (as indicated) were incubated for 20 minutes with 20 µl of the bacteria, N-formylmethionyl-leucyl-phenylalanine (fMLP), phorbol 12-myristate 13-acetate (PMA) or without stimulus at 37° C. Formation of the reactive oxidants during the oxidative burst was monitored by the addition and oxidation of dihydrorhodamine 123. To identify neutrophils, cells were stained with anti-CD16-PE antibody (IOTest®, Beckman Coulter) and analysed by fluorescence activated cell sorting. (FACS), (Becton Dickinson FACScan, San Jose, Calif.) using Cellquest™ software. Neutrophils were gated on forward and side scatter characteristics (FIG. 1A) and subsequently the percentage of CD16 positive cells producing reactive oxygen metabolites determined by green fluorescence (FL-1) measurement (FIGS. 1C, E, G). Samples were analyzed in triplicate of duplicate. The interassay coefficient of variation (CV) for resting burst was 5.4%, for stimulated burst 4.2%, the intraassay CV for resting burst was 4.7%, for stimulated burst 2.4%.

Neutrophil Phagocytosis

The Phagotest® (Orpegen Pharma, Heidelberg, Germany) was used to measure the overall percentage of neutrophils showing phagocytosis and the individual cellular phagocytotic activity using FITC-labelled opsonized E. coli bacteria. 100 µl of whole blood or isolated neutrophils (as indicated below) were incubated with 20 µl of bacteria at 37° C. for 20 min while a negative control sample remained on ice. To identify neutrophils, cells were stained with anti-CD-16-PE antibody (IOTest®, Beckman Coulter) Neutrophils were gated on forward and side scatter (FIG. 2A) characteristics and subsequently the percentage of CD16 positive cells—FITC positive cells, corresponding to the percentage of neutrophils undergoing phagocytosis and the geometric mean of fluorescence intensity (GMFI), corresponding to the number of bacteria engulfed by one cell, was analyzed (FIGS. 1B, D, F). To avoid misinterpretation of results due to batch-to-batch variability of bacteria, results are normalized to the mean of at least 3 healthy control samples for each new batch of bacteria used. Samples were analyzed in triplicate of duplicate. The interassay CV for percentage of phagocytosis was 6.8%, for GMFI 10.1% the respective intraassay CV for percentage of phagocytosis was 4.1%, and 1.6% for GMFI Neutrophil Isolation 4 ml of whole blood were layered over 5 ml of Polymorphoprep (Axis-Shield, Oslo, Norway) and spun for 30 min at 400 g, at room temperature. Neutrophils were harvested from the second interface and washed with PBS ((Sigma Aldrich, St. Louis, Mo., USA). Neutrophils are counted in a Thoma-hemocytometer and resuspended in PBS at a density of $5 \times 10^6$ cells in 50 µL. 50 µL of cell suspension and 50 µL of plasma were used for one assay. Viability was tested by Trypan Blue exclusion and was over 98%.

Endotoxin Removal Columns

Detoxi-Gel Affinity-pack prepacked columns (Pierce Biotechnology, Rockford, Ill.) containing an endotoxin removal gel consisting of immobilised polymixin B that binds to the lipid A portion of bacterial lipopolysaccharide were used to remove endotoxin from plasma samples. The columns were regenerated with 1% sodium deoxycholate (Sigma Aldrich, St. Louis, Mo., USA), washed with sterile water and equilibrated with sterile sodium chloride 0.9% supplemented with 501 U/ml of heparin (Multipharm, Waxham, UK) at room temperature. Plasma samples are diluted 1:1 with PBS and applied on the column and after discarding the void the sample was collected in a pyrogen free sample tube. 150 µL of this endotoxin-free, diluted plasma sample were incubated with 50 µL of cell suspension and Bursttest® or Phagotest® was performed as indicated.

Cytokines

TNFα, sTNFαR1, sTNFαR2, IL-6 and IL-8 were determined from ethylene-diamine-tetraacetate anticoagulated plasma samples using commercially available sets (BioSource International, Nivelles, Belgium) following the manufacturer's instructions. The lower limit for the detection of the cytokines was 3 pg/mL. The intra-assay coefficient of variation was 5.4% to 6.4%. IL-6 and IL-8 were undetectable in controls.

TABLE 1

|  | all (n = 63) | low resting burst (n = 35) | high resting burst (n = 28) |
|---|---|---|---|
| Death (%) | 22 | 9 | 42 |
| Organ failure (%) | 26 | 12 | 43 |
| Age (years) | 50.3 ± 1.3 | 52.4 ± 2.0 | 47.8 ± 1.6 |
| Liver function | | | |
| Bilirubin (mmol/L) | 151.2 ± 20.9 | 104.8 ± 21.8 | 199.8 ± 34.8[1] |
| PT (sec) | 15.3 ± 0.61 | 13.5 ± 0.5 | 16.8 ± 0.9[1] |
| Albumin (g/L) | 29.8 ± 1.1 | 32.7 ± 1.3 | 28.8 ± 1.3[1] |
| Maddrey's DF (n = 23 with AH) | 43.4 ± 6.8 | 40.0 ± 9.5 | 44.6 ± 8.0 |
| Pugh score | 9.3 ± 0.4 | 8.3 ± 0.4 | 10.2 ± 0.5[1] |
| MELD | 15.6 ± 1.8 | 12.2 ± 2.0 | 19.1 ± 3.5 |
| Priming (response to fMLP) | 57.5 ± 5.1 | 47.5 ± 7.9[2] | 89.1 ± 3.2[1,2] |
| Cytokine/Inflammation | | | |
| TNFα (pg/mL) | 19.6 ± 6.5 | 18.3 ± 6.9 | 22.3 ± 14.6 |
| IL-6 (pg/mL) | 49.4 ± 14.9 | 21.9 ± 7.9 | 106.1 ± 39.6 |
| IL-8 (pg/mL) | 180.5 ± 56.9 | 101.8 ± 55.8 | 337.9 ± 122.8 |
| Oxidative Stress | | | |
| MDA (µM/L) | 3.2 ± 0.5 | 3.2 ± 0.58 | 3.0 ± 0.7 |
| Prostaglandin F2α (pg/mL) | 346.8 ± 49.6 | 296.9 ± 43.8 | 394.7 ± 81.2 |

[1]significant versus low burst
[2]significant versus control

TABLE 2

|  | Child C (n = 27) | Child B (n = 26) | Child A (n = 10) | control (n = 13) |
|---|---|---|---|---|
| resting burst % | 67.0 ± 6.5[1,2,3] | 38.2 ± 7.2[1,3] | 36.0 ± 9.0[1] | 8.9 ± 2.7 |
| burst after stimulation - resting burst % | 32.4 ± 6.8[1,2,3] | 57.5 ± 7.0[1,3] | 60.4 ± 8.7[1] | 76.8 ± 7.7 |
| phagocytosis % | 105.9 ± 2.8 | 110.18 ± 3.3 | 107 ± 5.5 | 99.4 ± 7.5 |
| GMFI % | 50.7 ± 9.5[1] | 87.1 ± 13.6 | 104.6 ± 17.1 | 101.0 ± 9.2 |

[1]p < 0.05 versus control
[2]p < 0.05 versus Child B
[3]p < 0.05 versus Child A TABLE OF INFECTIONS
Documented culture positive infections in patients studied

| | high burst | | | | | low burst | | | |
| --- | --- | --- | --- | --- | --- | --- | --- | --- | --- |
| | first organism | | second organism | | | first organism | | second organism | |
| patient | day | organism | day | organism | patient | day | organism | day | organism |
| 1 | 4 | EC | 29 | MRSA | 2 | 16 | EC | | |
| 4 | 14 | EC | 19 | CNS | 14 | 23 | *E. coli* | | |
| 5 | 9 | CNS | 34 | EC | 17 | 9 | MRSA | | |
| 7 | 4 | EC | 10 | CNS | 23 | 15 | St. *aureus* | | |
| 12 | 2 | *C. albicans* | | | 33 | 15 | *Propionibacterium* | 34 | CNS |
| 13 | 10 | St. *aureus* | | | | | | | |
| 15 | 8 | CNS | | | | | | | |
| 20 | 5 | EC | 5 | CNS | | | | | |
| 35 | 6 | EC | | | | | | | |
| 36 | 4 | CNS | 4 | EC | | | | | |
| 45 | 2 | CNS | 3 | CNS | | | | | |
| 48 | 20 | *E. coli* | | | | | | | |
| 61 | 6 | *C. albicans* | | | | | | | |
| 62 | 7 | *C. albicans* | 9 | EC | | | | | |

EC: *Enterococcus*,
MRSA: methicillin-resistant *Staphylococcus aureus*,
CNS: coagulase-negative *Staphylococcus*,
St.: *Staphylococcus*,
Str.: *Streptococcus*,
C.: *Candidia*

The invention claimed is:

1. A method for assessing prognosis in an individual suffering from alcoholic cirrhosis, which method comprises:
   (a) (i) contacting a plasma sample from the individual with a population of neutrophils not from the individual to produce a test population of neutrophils, and
      (ii) providing a control sample comprising a population of neutrophils from another individual having a normal liver function wherein said control sample is not contacted with said plasma sample;
   (b) assessing the ability of the test population of neutrophils of (a)(i) to phagocytose; and
   (c) comparing said ability of said test population to phagocytose with the ability of said control sample of neutrophils of (a)(ii) to phagocytose;
   wherein a lower level of neutrophil phagocytosis in said test population, as compared with the level of neutrophil phagocytosis in said control sample is indicative of a prognosis of at least one condition selected from the group consisting of organ failure and mortality.

2. A method according to claim 1 wherein said control sample of (a)(ii) is a whole blood sample or a fraction of a whole blood sample comprising said population of neutrophils.

3. A method according to claim 1, wherein step (b) comprises assessing at least one selected from the group consisting of:
   (i) overall number of neutrophils within the sample that show phagocytosis;
   (ii) proportion of neutrophils within the sample that show phagocytosis;
   (iii) total number of bacteria that are phagocytosed when contacted with the sample of neutrophils; and
   (iv) number of cells that an individual neutrophil or a population of neutrophils are able to phagocytose.

4. A method according to claim 1, wherein the method further comprises:
   (a) labelling material to be phagocytosed;
   (b) allowing phagocytosis to occur; and
   (c) quantifying and/or locating the label to indicate the amount of phagocytosis that has occurred.

5. A method according to claim 4, wherein said material to be phagocytosed is cells.

6. A method according to claim 4, wherein said labelled material to be phagocytosed is FITC-labelled opsonized *E. coli* bacteria.

7. A method according to claim 1, wherein the individual suffering from alcoholic cirrhosis is also suffering from at least one condition selected from the group consisting of:
   (a) chronic liver failure;
   (b) alcoholic liver disease; and
   (c) alcoholic hepatitis.

8. A method according to claim 1, wherein said organ failure comprises kidney failure.

9. A method according to claim 1, wherein said organ failure comprises multiorgan failure.

10. A method according to claim 9, wherein said multiorgan failure comprises respiratory failure.

11. A method according to claim 9, wherein said multiorgan failure comprises cardiovascular failure.

* * * * *

UNITED STATES PATENT AND TRADEMARK OFFICE
CERTIFICATE OF CORRECTION

| | | |
|---|---|---|
| PATENT NO. | : 8,415,117 B2 | Page 1 of 1 |
| APPLICATION NO. | : 12/311605 | |
| DATED | : April 9, 2013 | |
| INVENTOR(S) | : Jalan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this
Seventeenth Day of February, 2015

Michelle K. Lee
*Deputy Director of the United States Patent and Trademark Office*